US009469725B2

(12) United States Patent
Levins et al.

(10) Patent No.: US 9,469,725 B2
(45) Date of Patent: Oct. 18, 2016

(54) ULTRAVIOLET RADIATION ABSORBING POLYMERS

(71) Applicant: JOHNSON & JOHNSON CONSUMER INC., Skillman, NJ (US)

(72) Inventors: Christopher G. Levins, Flemington, NJ (US); Aruna Nathan, Bridgewater, NJ (US); Susan Daly, Basking Ridge, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 13/799,193

(22) Filed: Mar. 13, 2013

(65) Prior Publication Data

US 2014/0004060 A1      Jan. 2, 2014

Related U.S. Application Data

(60) Provisional application No. 61/665,430, filed on Jun. 28, 2012.

(51) Int. Cl.
    *C08G 63/685*      (2006.01)
    *A61Q 17/04*       (2006.01)
    *A61K 8/85*        (2006.01)
    *C08G 63/54*       (2006.01)

(52) U.S. Cl.
    CPC ............ *C08G 63/6856* (2013.01); *A61K 8/85* (2013.01); *A61Q 17/04* (2013.01); *C08G 63/54* (2013.01); *A61K 2800/57* (2013.01)

(58) Field of Classification Search
    None
    See application file for complete search history.

(56) References Cited

U.S. PATENT DOCUMENTS

| | | |
|---|---|---|
| 4,107,290 A | 8/1978 | Jacquet et al. |
| 4,322,522 A | 3/1982 | Johnson et al. |
| 4,399,297 A | 8/1983 | Thoemel et al. |
| 4,528,311 A | 7/1985 | Beard et al. |
| 4,839,160 A | 6/1989 | Forestier et al. |
| 4,897,259 A | 1/1990 | Murray et al. |
| 5,039,782 A | 8/1991 | Langer et al. |
| 5,138,089 A | 8/1992 | Sabatelli |
| 5,157,091 A | 10/1992 | Masataka et al. |
| 5,166,234 A | 11/1992 | Kawaguchi et al. |
| 5,250,652 A | 10/1993 | Langer et al. |
| 5,399,371 A | 3/1995 | Harris |
| 5,459,222 A | 10/1995 | Rodgers et al. |
| 5,487,885 A | 1/1996 | Sovak et al. |
| 5,585,090 A | 12/1996 | Yoshioka et al. |
| 5,741,924 A | 4/1998 | Sovak et al. |
| 5,843,410 A | 12/1998 | Kim et al. |
| 5,869,030 A | 2/1999 | Dumler et al. |
| 5,869,099 A | 2/1999 | Keller et al. |
| 6,001,337 A | 12/1999 | Keller et al. |
| 6,048,516 A | 4/2000 | Bringhen et al. |
| 6,123,928 A | 9/2000 | Sovak et al. |
| 6,143,850 A | 11/2000 | Keller et al. |
| 6,183,728 B1 | 2/2001 | Forestier et al. |
| 6,193,959 B1 | 2/2001 | Bernasconi et al. |
| 6,294,156 B1 | 9/2001 | Lentini et al. |
| 6,391,287 B1 | 5/2002 | Baldo et al. |
| 6,413,393 B1 | 7/2002 | Van Antwerp et al. |
| 6,471,949 B2 | 10/2002 | Candau et al. |
| 6,540,986 B2 | 4/2003 | Lukenbach et al. |
| 6,620,407 B1 | 9/2003 | Gers-Barlag et al. |
| 6,620,904 B2 | 9/2003 | Lemke |
| 6,767,547 B2 | 7/2004 | Gers-Barlag et al. |
| 6,800,274 B2 | 10/2004 | Bonda et al. |
| 6,814,959 B1 | 11/2004 | Muller et al. |
| 6,867,250 B1 | 3/2005 | Gupta et al. |
| 6,869,597 B2 | 3/2005 | Arnaud |
| 6,881,415 B1 | 4/2005 | Gers-Barlag et al. |
| 6,899,866 B2 | 5/2005 | Bonda |
| 6,905,674 B2 | 6/2005 | L'Alloret |
| 6,951,911 B2 | 10/2005 | Tagawa et al. |
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |
| 7,465,438 B2 | 12/2008 | Schunicht et al. |
| 7,534,420 B2 | 5/2009 | Bonda et al. |
| 7,749,524 B2 | 7/2010 | Lu et al. |

(Continued)

FOREIGN PATENT DOCUMENTS

| | | |
|---|---|---|
| EP | 407932 A | 1/1991 |
| EP | 413648 A | 2/1991 |

(Continued)

OTHER PUBLICATIONS

Stiriba et al., "Hyperbranched molecular nanocapsules: Comparison of the hyperbranched architecture with the perfect linear analogue", *Journal of the American Chemical Society* (2002) vol. 124, pp. 9698-9699.

Li et al., "Synthesis of polyethylene glycol (PEG) derivatives and PEGylated-peptide biopolymer conjugates", *Biomacromolecules*, American Chemical Society, US, vol. 4, No. 4, May 17, 2003, pp. 1055-1067 (XP002328259), (ISSN: 1525-7797, DOI: 10.1021/BM034069L).

Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.

(Continued)

*Primary Examiner* — Jianfeng Song

(57) ABSTRACT

The present invention includes an ultraviolet radiation absorbing polymer composition that includes polymers containing a UV-chromophore, as described in the specification and as claimed the reaction product of a monoglyceride and a poly-acid monomer containing a UV-chromophore.

12 Claims, No Drawings

(56) References Cited

U.S. PATENT DOCUMENTS

| | | | |
|---|---|---|---|
| 7,850,954 | B2 | 12/2010 | Leblanc et al. |
| 7,914,775 | B2 | 3/2011 | Cottard et al. |
| 7,988,953 | B2 | 8/2011 | Poschalko et al. |
| 7,993,680 | B2 | 8/2011 | Clemente et al. |
| 8,003,132 | B2 | 8/2011 | Clemente et al. |
| 8,025,868 | B2 | 9/2011 | Clemente et al. |
| 8,211,850 | B2 | 7/2012 | Andjelic et al. |
| 8,394,755 | B2 | 3/2013 | Andjelic et al. |
| 2001/0038829 | A1 | 11/2001 | Hasebe et al. |
| 2002/0131941 | A1 | 9/2002 | Habeck et al. |
| 2002/0155073 | A1 | 10/2002 | Fankhauser et al. |
| 2003/0165553 | A1 | 9/2003 | Gers-Barlag et al. |
| 2004/0019220 | A1 | 1/2004 | Fischer et al. |
| 2004/0022836 | A1 | 2/2004 | Degen et al. |
| 2004/0057914 | A1* | 3/2004 | Bonda et al. .................. 424/59 |
| 2004/0096406 | A1 | 5/2004 | De Poilly |
| 2004/0126339 | A1 | 7/2004 | Roszell |
| 2004/0197359 | A1 | 10/2004 | Yamada et al. |
| 2004/0223925 | A1 | 11/2004 | L'Alloret |
| 2004/0228814 | A1 | 11/2004 | Candau et al. |
| 2005/0031660 | A1 | 2/2005 | Deckner |
| 2005/0036961 | A1 | 2/2005 | Hansenne et al. |
| 2005/0048010 | A1 | 3/2005 | Kliss et al. |
| 2005/0065251 | A1 | 3/2005 | Candau et al. |
| 2005/0180933 | A1 | 8/2005 | Wei et al. |
| 2006/0204457 | A1 | 9/2006 | Toda et al. |
| 2007/0098653 | A1 | 5/2007 | Tamasawa et al. |
| 2007/0134174 | A1 | 6/2007 | Irwin et al. |
| 2008/0081025 | A1 | 4/2008 | Poschalko et al. |
| 2008/0089852 | A1 | 4/2008 | Hotz et al. |
| 2008/0247975 | A1 | 10/2008 | Dueva-Koganov et al. |
| 2008/0311234 | A1 | 12/2008 | Yoneda et al. |
| 2009/0016971 | A1 | 1/2009 | Gaudry et al. |
| 2009/0041688 | A1 | 2/2009 | Dueva-Koganov et al. |
| 2009/0068130 | A1 | 3/2009 | Spaulding et al. |
| 2009/0185988 | A1 | 7/2009 | Maleski et al. |
| 2009/0214460 | A9 | 8/2009 | Luukas |
| 2009/0232859 | A1 | 9/2009 | Sakuta et al. |
| 2009/0258230 | A1 | 10/2009 | Schlossman et al. |
| 2009/0297462 | A1 | 12/2009 | Hessefort et al. |
| 2009/0324523 | A1 | 12/2009 | Clemente et al. |
| 2009/0324524 | A1 | 12/2009 | Clemente et al. |
| 2010/0003202 | A1 | 1/2010 | Matsumoto et al. |
| 2010/0129303 | A1 | 5/2010 | Dueva-Koganov et al. |
| 2010/0189661 | A1 | 7/2010 | Musa et al. |
| 2010/0226867 | A1 | 9/2010 | Dueva-Koganov et al. |
| 2010/0239508 | A1 | 9/2010 | Mori et al. |
| 2010/0284948 | A1 | 11/2010 | Ohrmann et al. |
| 2011/0014139 | A1 | 1/2011 | Viala et al. |
| 2011/0027202 | A1 | 2/2011 | Candau et al. |
| 2011/0104078 | A1 | 5/2011 | Burgo et al. |
| 2011/0117034 | A1 | 5/2011 | Satonaka et al. |
| 2011/0195036 | A1 | 8/2011 | Clemente et al. |
| 2012/0058974 | A1 | 3/2012 | Misske et al. |
| 2012/0087882 | A1 | 4/2012 | Fevola et al. |
| 2012/0093753 | A1 | 4/2012 | Fevola et al. |
| 2012/0294813 | A1 | 11/2012 | Frey et al. |
| 2013/0115179 | A1 | 5/2013 | Janssen et al. |
| 2014/0004064 | A1 | 1/2014 | Daly |

FOREIGN PATENT DOCUMENTS

| | | |
|---|---|---|
| EP | 0523955 A | 1/1993 |
| EP | 601080 A | 7/1995 |
| EP | 681830 A | 11/1995 |
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| EP | 2679616 A | 1/2014 |
| JP | S6099186 A | 6/1985 |
| JP | 2006-265389 A | 10/2006 |
| JP | 2009-167168 A | 7/2009 |
| WO | 92/19592 A | 11/1992 |
| WO | WO 93/22366 A | 11/1993 |
| WO | WO 93/22413 A | 11/1993 |
| WO | WO 96/03369 A | 2/1996 |
| WO | WO 01/08647 A | 2/2001 |
| WO | WO 02/24668 A | 3/2002 |
| WO | WO 02/36534 A | 5/2002 |
| WO | WO 2004/009047 A | 1/2004 |
| WO | WO 2005/092282 A | 10/2005 |
| WO | WO2007066309 * | 6/2007 |
| WO | WO 2007/081209 A | 7/2007 |
| WO | WO 2008/056678 A | 5/2008 |
| WO | WO 2010/060776 A | 6/2010 |
| WO | WO 2010/115009 A | 10/2010 |
| WO | WO 2011/048570 A | 4/2011 |
| WO | WO 2011/070050 A | 6/2011 |
| WO | WO 2011/070053 A | 6/2011 |
| WO | WO 2011/070073 A | 6/2011 |
| WO | WO 2011/070075 A | 6/2011 |
| WO | WO 2011/070077 A | 6/2011 |
| WO | WO 2014/004474 A | 1/2014 |
| WO | WO 2014/004477 A | 1/2014 |

OTHER PUBLICATIONS

"Crodacol™ C95 Product Details" from the Croda website, 2013 http://www.croda.com/home.aspx?view=dtl&d=content&s=157&r=401&p=2578&prodID-1779.

Erberich et al., "Polyglycidols with Two Orthogonal Protective Groups: Preparation, Selective Deprotection, and Functionalization", *Macromolecules* (2007), vol. 40, pp. 3070-3079.

Fitton et al., Synthesis (1987), pp. 1140-1142.

Hanson et al., "Sunscreen Enhancement of UV-induced Reactive Oxygen Species in the Skin", *Free Radical Biology & Medicine* (2006) vol. 41, pp. 1205-1212.

Haouet et al., "Preparation Et Proprietes Des Poly®-Glycidols", *European Polymer Journal* (1983), vol. 19(12), pp. 1089-1098. (English Abstract).

Kuhn et al., "Monitoring the Kinetics of Ion-Dependent Protein Folding by Time-Resolved NMR Spectroscopy at Atomic Resolution", *Journal of the American Chemical Society* (2000), vol. 122, pp. 6169-6174.

Lee et al., "Poly(allyl Glycidyl Ether)—A Versatile and Functional Polyether Platform", *Journal of Polymer Science Part A: Polymer Chemistry* (2011), vol. 49, pp. 4498-4504.

Obermeier et al., "Poly(ethylene glycol-co-allyl glycidyl ether)s: A PEG-Based Modular Synthetic Platform for Multiple Bioconjugation", *Bioconjugate Chemistry* (2011), vol. 22, pp. 436-444.

Moore et al., "Room Temperature Polyesterification", *Macromolecules* (1990), vol. 23, Issue 1, pp. 65-70.

Rokicki et al., "Hyperbranched aliphatic polyethers obtained from environmentally benign monomer: glycerol carbonate", *Green Chemistry* (2005), vol. 7, pp. 529-539.

Sunder et al., "Controlled Synthesis of Hyperbranched Polyglycerols by Ring-Opening Multibranching Polymerization", *Macromolecules* (1999), vol. 32, pp. 4240-4246.

Taton et al., "Synthesis of chiral and racemic functional polymers from glycidol and thioglycidol", *Macromolecular Chemistry and Physics* (1994), vol. 195, pp. 139-148.

Tchao, "Trans-Epithelial Permeability of Fluorescein in Vitro as an Assay to Determine Eye Irritants", *Alternative Methods in Toxicology 6, Progress in In Vitro Toxicology* (ed. A.M. Goldberg) (1988), pp. 271-283.

Tokar et al., "Cationic Polymerization of Glycidol: Coexistence of the Activated Monomer and Active Chain End Mechanism", *Macromolecules* (1994), vol. 27, pp. 320-322.

U.S. Appl. No. 13/926,248, filed Jun. 25, 2013, Daly.
U.S. Appl. No. 13/926,282, filed Jun. 25, 2013, Daly.
U.S. Appl. No. 61/665,464, filed Jun. 28, 2012, Daly et al.
U.S. Appl. No. 13/535,890, filed Jun. 28, 2012, Daly et al.
U.S. Appl. No. 13/710,531, filed Dec. 11, 2012, Daly et al.
U.S. Appl. No. 13/535,899, filed Jun. 28, 2012, Daly et al.
U.S. Appl. No. 13/710,546, filed Dec. 11, 2012, Daly et al.
U.S. Appl. No. 13/535,909, filed Jun. 28, 2012, Daly et al.

(56) References Cited

OTHER PUBLICATIONS

U.S. Appl. No. 13/710,555, filed Dec. 11, 2012, Daly et al.
U.S. Appl. No. 61/665,430, filed Jun. 28, 2012, Levins et al.
U.S. Appl. No. 61/665,439, filed Jun. 28, 2012, Levins et al.
U.S. Appl. No. 13/799,222, filed Mar. 13, 2013, Levins et al.

* cited by examiner

ULTRAVIOLET RADIATION ABSORBING POLYMERS

This application claims the benefit of U.S. provisional application 61/665,430 filed Jun. 28, 2012, the complete disclosure of which is hereby incorporated herein by reference for all purposes.

FIELD OF THE INVENTION

The invention relates to polymers bearing a chromophore suited for the absorption of ultraviolet radiation.

BACKGROUND OF THE INVENTION

Skin cancer is a significant public health concern which represents 50% of diagnosed cases of cancer in the United States. Ultraviolet radiation (UV) can cause molecular and cellular level damage, and is considered the leading environmental factor responsible for skin cancer. The prolonged exposure to UV radiation, such as from the sun, can lead to the formation of light dermatoses and erythemas, as well as increase the risk of skin cancers, such as melanoma, and accelerate skin aging processes, such as loss of skin elasticity and wrinkling.

The damaging effects of UV exposure can be suppressed by topical application of sunscreens which contain compounds that absorb, reflect or scatter UV, typically in the UVA (wavelengths from about 320 to 400 nm) or UVB (wavelengths from around 290 to 320 nm) range of the spectrum. Numerous sunscreen compounds are commercially available with varying ability to shield the body from ultraviolet light.

It has been suggested to use sunscreen molecules having high molecular weights in order to reduce the penetration of the sunscreen molecule through the epidermis. However, the inventors have recognized that it would be desirable to have entirely new polymeric sunscreen compounds (ultraviolet radiation-absorbing polymers) in order to provide any of various benefits such as improved protection from UV.

SUMMARY OF THE INVENTION

The present invention includes ultraviolet radiation absorbing polymers that include a repeat unit as shown below:

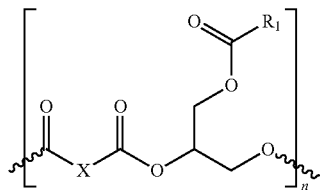

wherein X comprises a UV absorbing chromophore, and $R_1$ is a saturated or unsaturated hydrocarbon moiety having a number of carbon atoms between 4 and 30; ultraviolet radiation absorbing polymers that include the reaction product of a monoglyceride and a poly-acid monomer containing a UV-chromophore and compositions that include ultraviolet radiation absorbing polymers of the present invention and a cosmetically-acceptable carrier.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever. Unless defined otherwise, all technical and scientific terms used herein have the same meaning as commonly understood by one of ordinary skill in the art to which the invention belongs. Also, all publications, patent applications, patents, and other references mentioned herein are incorporated by reference.

UV Absorbing Polymer

Embodiments of the invention relate to polymer compositions including an ultraviolet radiation absorbing polymer, (i.e., "UV absorbing polymer"). By "UV absorbing polymer," it is meant a polymer that absorbs radiation in some portion of the ultraviolet spectrum (wavelengths between 290 and 400 nm). The UV absorbing polymer composition has a molecular weight ($M_w$), which may be suitable for reducing or preventing the UV-chromophore from absorbing through the skin. According to one embodiment, a suitable molecular weight for the UV absorbing polymer is $M_w$ greater than 500. In one embodiment, $M_w$ is in the range from about 500 to about 50,000. In another embodiment, the UV absorbing polymer composition has an $M_w$ from about 4000 to about 12,000.

According to one aspect of the invention, the polymer composition includes a UV absorbing polymer having a repeat unit as shown below in Formula 1A:

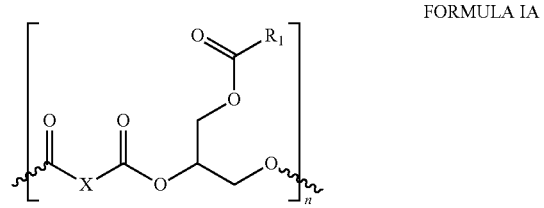

FORMULA IA

A "repeat unit", as defined herein and known in the art, is the smallest atom or group of atoms (with pendant atoms or groups, if any) comprising a part of the essential structure of a macromolecule, oligomer, block, or chain, the repetition of which constitutes a regular macromolecule, a regular oligomer molecule, a regular block, or a regular chain.

In Formula IA, X comprises a UV absorbing moiety, or a structure with a pendant UV absorbing moiety (UV-chromophore), such as a UVA absorbing moiety. $R_1$ is a saturated or unsaturated hydrocarbon moiety having a number of carbon atoms between 4 and 30; in one embodiment, the number of carbon atoms is between 12 and 18. Further, subscript "n" indicates the number of repeat units in the polymer chain.

The UV-chromophore may be part of the polymer backbone, or may be pendant to the polymer backbone. As will be recognized by those of skill in the art, the "backbone" refers generally to that portion of the polymer molecule having the largest number of continuous and covalently bonded atoms. Other smaller groups of covalently bonded atoms are considered pendant groups that branch from the backbone.

According to one embodiment, the UV absorbing polymer composition includes a polymer having a structure as shown below in FORMULA I.

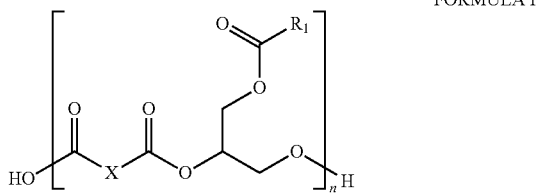

FORMULA I

According to another embodiment, the UV absorbing polymer composition includes a branched polymer, shown below in FORMULA II.

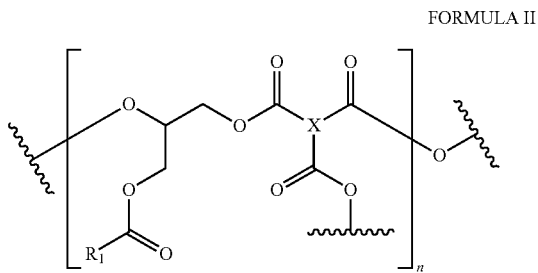

FORMULA II

Some UV-chromophores have a single functional group suitable for covalent attachment to a polymer. Examples of these functional groups include, but are not limited to, carboxylic acids, amines, alcohols, thiols, and isocyanates. These UV-chromophores can be covalently attached as pendant groups to polymers like those illustrated in FORMULA I and FORMULA II using various approaches. Two embodiments are described herein: covalent attachment of a UV-chromophore to a polymer backbone, and polymerization of monomers with pendant UV-chromophores.

According to another embodiment, the UV absorbing polymer composition is the reaction product of a monoglyceride and a poly-acid monomer containing a UV-chromophore. In one embodiment, the UV-chromophore contains a single functional group attached covalently to complimentary functional groups on the polymer. In one embodiment, a polymer is synthesized through polycondensation of a monoglyceride with a poly-acidic monomer, i.e., has at least two carboxylic acid groups, that contains an additional functional group. The additional functional group is incorporated into the polymer, and provides a site for covalent attachment of the UV-chromophore to the polymer. Examples of functional groups that are sites for covalent attachment of UV-chromophores include, but are not limited to, conjugated alkenes, amines, alcohols, and carboxylic acids.

A monoglyceride is defined herein as a derivative of glycerol containing a single long chain. e.g., from 4 up to and including 30 carbon atoms, such as from 12 up to and including 18 carbon atoms, alkyl ester. Suitable monoglycerides include, but are not limited to, glycerol monostearate, glycerol monopalmitate, glycerol monomyristate, glycerol monocaprate, glycerol monodecanoate, glycerol monolaurate, glycerol monolinoleate, glycerol monooleate, and combinations thereof. In one embodiment, the monoglyceride is glycerol monolaurate.

Examples of poly-acidic monomers with conjugated alkene functional groups include maleic, fumaric, itaconic and citraconic acids. UV-chromophores functionalized with amines or thiols, for example, can covalently bond to these alkene groups in polymers through conjugate addition reactions. Polymers containing amines or hydroxyl groups are synthesized by polycondensation of monoglycerides with poly-acidic monomers containing amine or hydroxyl functional groups. The amine or hydroxyl groups are masked to prevent interference with the polymerization reaction using protecting groups known to those skilled in the art. The protecting groups are removed following polymerization. In the case of polymers containing free hydroxyl or amine groups, a UV-chromophore containing a carboxylate group may be covalently attached to the polymer using a number of methods familiar to those skilled in the art. Condensation reagents can be used to form covalent bonds between UV-chromophores with carboxylic acids and amine or hydroxyl groups on polymers, generating amide and ester bonds, respectively; in one embodiment, the condensation reagent is N-(3-dimethylaminopropyl)-N'-ethylcarbodiimide hydrochloride. The carboxylic acid of the UV-chromophore may also be attached to hydroxyl groups on the polymer through ester bonds using transition metal catalysts. In one embodiment, the catalyst is tin (II) ethylhexanote. The UV-chromophore can also be attached to the polymer by converting the UV-chromophore carboxylic acid to the corresponding acid chloride. The acid chloride reacts with amine or hydroxyl groups on the functional polymer forming amide or ester bonds, respectively. In one embodiment, this conversion to the acid chloride is performed using thionyl chloride. The UV-chromophore carboxylic acid may also be converted to the isocyanate through Curtius rearrangement of an intermediate acid azide. The UV-chromophore isocyanate reacts with amine or hydroxyl groups on the functional polymer forming urea or urethane bonds, respectively.

In the second embodiment, the UV-chromophore containing a single functional group is chemically modified. The product of the modification contains two or more carboxylic acid functional groups, and can participate in polycondensation polymerization with monoglycerides. Molecules which can be used to chemically modify UV-chromophores to generate structures with multiple carboxylic acid groups include, but are not limited to, iminodiacetic acid, aminoisophthalic acid, glutamic acid, and aminomalonic acid. In one embodiment, the molecule which can be used to generate structures with multiple carboxylic acid groups is iminodiacetic acid. The reaction product of a UV-chromophore containing a carboxylic acid and iminodiacetic acid is illustrated by structure "A" in FORMULA III. One skilled in the art will recognize that the molecule represented by structure "A" can be synthesized by activating the carboxylic acid on the UV-chromophore using various means, including condensation reagents, and activation using chlorinating reagents such as thionyl chloride. Alternatively, the carboxylic acid on the UV-chromophore may be converted to the isocyanate through Curtius rearrangement of an intermediate acid azide. The reaction of this isocyante with the amine of iminodiaectic acid would generate a product represented by structure "B" in FORMULA III.

FORMULA III

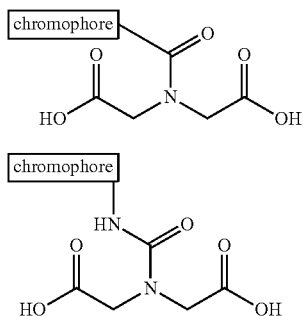

Suitable UV-chromophores include those that have absorbance of UVA radiation; other suitable UV-chromophores are those which have absorbance in the UVB region. In one embodiment, the UV-chromophore absorbs in both the UVA and UVB region. In one embodiment, when the UV-absorbing polyether is cast into a film, it is possible to generate a molar extinction coefficient measured for at least one wavelength in this wavelength range of at least about 1000 $mol^{-1}$ $cm^{-1}$, preferably at least about 2000 $mol^{-1}$ $cm^{-1}$, more preferably at least about 4000 $mol^{-1}$ $cm^{-1}$. In one embodiment, the molar extinction coefficient among at least 40% of the wavelengths in this portion of the spectrum is at least about 1000 $mol^{-1}$ $cm^{-1}$. Examples of UV-chromophores that are UVA absorbing include triazoles such as benzotriazoles; camphors such as benzylidene camphor and its derivatives (such as terephthalylidene dicamphor sulfonic acid); dibenzoylmethanes and their derivatives. By triazole, it is meant a moiety containing a five-membered heterocyclic ring with two carbon and three nitrogen atoms.

In one embodiment, the UV-chromophore is a benzotriazole, such as a benzotriazole providing both photostability and strong UV-A absorbance with a structure represented in FORMULA IV:

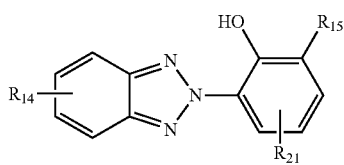

wherein $R_{14}$ is independently selected from the group consisting of hydrogen, $C_1$-$C_{20}$ alkyl, alkoxy, acyl, alkyloxy, alkylamino, and halogen; $R_{15}$ is independently selected from the group consisting of hydrogen, $C_1$-$C_{20}$ alkyl, alkoxy, acyl, alkyloxy, and alkylamino; and $R_{21}$ is selected from $C_1$-$C_{20}$ alkyl, alkoxy, acyl, alkyloxy, and alkylamino. Either of the $R_{15}$ or $R_{21}$ groups may include functional groups that allow attachment to a polymer, or allow for participation in condensation polymerization reactions. Monomeric compounds of FORMULA IV are described in U.S. Pat. No. 5,869,030, and include, but are not limited to, methylene bis-benzotriazolyl tetramethylbutylphenol (a compound sold under the trade name TINSORB M by BASF Corporation, Wyandotte, Mich.). In one embodiment, the UV absorbing triazole is a transesterification product of 3-(3-(2H-benzo[d][1,2,3]triazol-2-yl)-5-(tert-butyl)-4-hydroxyphenyl) propanoic acid with polyethylene glycol 300, commercially available under the trade name TINUVIN 213, also available from BASF. In another embodiment, the UV chromophore is a triazine moiety. By triazine, it is meant a six membered heterocycle containing three nitrogen and three carbon atoms. An exemplary triazine is 6-octyl-2-(4-(4,6-di([1,1'-biphenyl]-4-yl)-1,3,5-triazin-2-yl)-3-hydroxyphenoxy)propanoate (a compound sold under the trade name TINUVIN 479 by BASF Corporation, Wyandotte, Mich.).

In another embodiment, the UV-chromophore is a UVB absorbing moiety. By UV absorbing it is meant that the UV-chromophore has appreciable absorbance in the UVB portion (290 to 320 nm) of the ultraviolet spectrum. In one embodiment, the criteria for consideration as a UVB absorbing chromophore is similar to those described above for an UVA absorbing chromophore, except that the wavelength range is 290 nm to 320 nm.

Examples of suitable UVB absorbing chromophores include 4-aminobenzoic acid and alkane esters thereof; anthranilic acid and alkane esters thereof; salicylic acid and alkane esters thereof; hydroxycinnamic acid and alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; benzalmalonate (benzylidene malonate); benzimidazole derivatives (such as phenyl benzilimazole sulfonic acid, PBSA), benzoxazole derivatives, and other suitably functionalized species capable of copolymerization within the polymer chain.

In some cases, the UV-chromophore may have two or more carboxylic acid functional groups suitable for polymerization with monoglycerides. In these cases, the UV-chromophore will be incorporated into the backbone of the polymer. On polymerization, UV-chromophores that contain three or more carboxylic acids are expected to generate branched structures, as illustrated in FORMULA II. In one embodiment, the UV-chromophore is the product of base promoted hydrolysis of trioctyl 2,2',2"-(((1,3,5-triazine-2,4,6-triyl)tris(3-hydroxybenzene-4,1-diyl))tris(oxy))tripropanoate (a UV-chromophore sold under the trade name TINUVIN 477 by BASF Corporation, Wyandotte, Mich.).

The UV absorbing polymer may optionally further incorporate other poly-ols, i.e. moieties that have at least two hydroxyl groups, in addition to the monoglyceride, in the interest of optimizing the material properties. Suitable poly-ols include, but are not limited to, ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s glycols, polyglycerols, polyglycerol esters, glycerol, monosaccharide, disaccharides, and polysaccharides. Suitable poly-ols also include linear polysiloxanes end-functionalized with carbinol groups, the number of siloxane linkages (—Si—O—) in the backbone of the polymer ranging from 1 to about 100. In one embodiment, the number of siloxane linkages is between 5 and 50.

The UV absorbing polymer may optionally further include other poly-acids in addition to the poly-acid monomer containing a UV-chromophore, in the interest of optimizing the material properties. Suitable poly-acids include, but are not limited to, natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Poly-acid derivatives include anhydrides, such as succinic anhydride, diglycolic anhydride, glutaric anhydride and maleic anhydride, mixed anhydrides, esters, activated esters and acid halides. In one embodiment, the poly-acid is succinic acid. In another embodiment, the poly-acid is sebacic acid.

Alternative embodiments of the UV absorbing polymer are shown in FORMULA V:

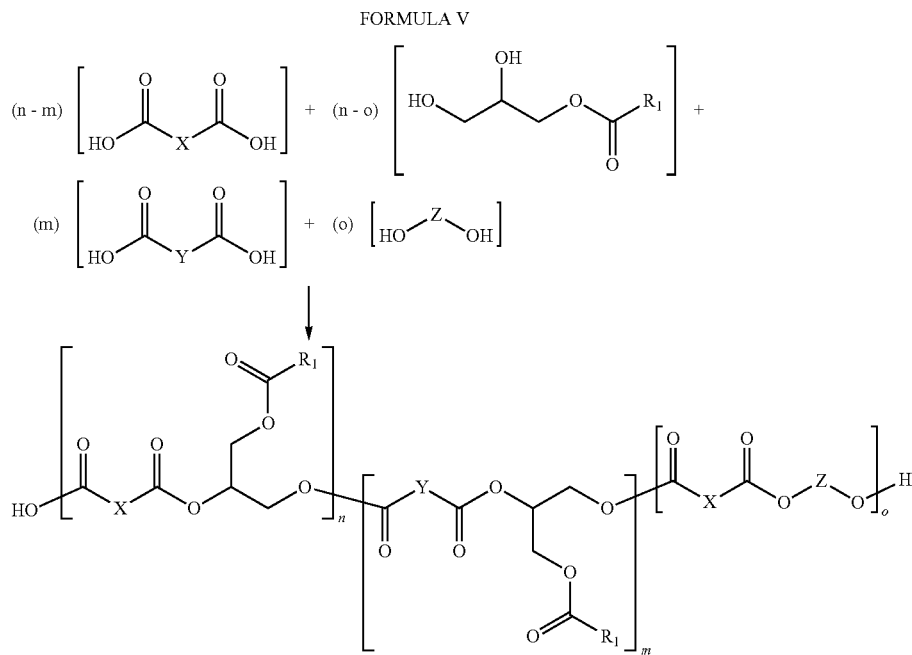

FORMULA V wherein X and $R_1$ are defined as described above for FORMULA I and FORMULA II; n, m and o are real numbers indicating the number of each of the repeat units shown in FORMULA V above, where (n-m), (n-o), (m) and (o) represent, for example, the molar feed ratio of the various components; the monomer containing structure Y representing the structure from additional poly-acids such as those defined above; the monomer containing structure Z representing the structure resulting from the use of additional poly-ols as defined above.

In one embodiment, a UV absorbing polymer composition is prepared by the polycondensation of the monoglyceride with the poly-acid containing a UV-chromophore by melt polymerization. The polymerization of the monoglyceride, poly-acid containing a UV-chromophore, and in some cases with other poly-ols and poly-acids, is performed in the presence of an organometallic catalyst at elevated temperatures. In one embodiment, the catalyst is a tin-based catalyst, e.g. tin (II) ethyl hexanoate. In one embodiment, the molar feed ratios of the poly-acid containing a UV-chromophore, monoglyceride, other poly-acid and other poly-ol are such that n equals 1, and m and o (FORMULA V) are equal to or between 0 and 0.9. In another embodiment, n equals 1, and both m and o are equal to 0. The catalyst will be present in the mixture at a mole ratio of poly-ol and polycarboxylic acid to catalyst in the range of from about 100/1 to 100,000/1. In one embodiment the catalyst will be present in the range of 1000/1 to 10,000/1. The melt polymerization reaction is performed at a temperature between 120° C. and 240° C. In one embodiment, the polymerization is performed at about 180° C. The polymerization reaction is allowed to proceed at this temperature from about 15 minutes to about 72 hours. In one embodiment, the reaction is performed for about 4 hours.

In another embodiment, the polymerization of the monoglyceride, poly-acid containing a UV-chromophore, and in some cases other poly-ols and poly-acids, is prepared by solution polymerization using condensation reagents. Condensation reagents include, but are not limited to, 1-ethyl-3-(3'-dimethylaminopropyl)carbodiimide, dicyclohexylcarbodiimide, diisopropylcarbodiimide, benzotriazole-1-yloxy-tris-(dimethylamino)-phosphonium hexafluorophosphate, O-(7-Azabenzotriazol-1-yl)-N,N,N',N'-tetramethyluronium hexafluorophosphate, 1,1'-carbonyldiimidazole, 1-[(1-(Cyano-2-ethoxy-2-oxoethylideneaminooxy)dimethylaminomorpholino)]uronium hexafluorophosphate, 3-(diethoxy-phosphoryloxy)-1,2,3-benzo[d]triazin-4(3H)-one, N,N'-Disuccinimidyl carbonate, 2-(1H-Benzotriazole-1-yl)-1,1,3,3-tetramethyluronium hexafluorophosphate, O-(1H-6-Chlorobenzotriazole-1-yl)-1,1,3,3-tetramethyluronium hexafluorophosphate, 6-Chlorobenzotriazole-1-yloxy-tris-pyrrolidinophosphonium hexafluorophosphate, and 2-(1H-Benzotriazole-1-yl)-1,1,3,3-tetramethylaminium tetrafluoroborate. In one embodiment, the condensation reagent is diisopropylcarbodiimide.

The condensation polymerization is performed in solution using an organic nucleophilic catalyst. In one embodiment, the catalyst is dimethylaminopyridine. In another embodiment, the catalyst is the 1:1 salt of dimethylaminopyridine and para-toluene sulfonic acid.

The reaction is performed in the range of −20° C. to 100° C. In one embodiment, the reaction is performed between 25° C. and 50° C. Suitable solvents for the reaction include, but are not limited to, acetone, acetonitrile, benzene, dichloromethane, diglyme ethyl acetate, glyme, pyridine, tetrahydrofuran and triglyme. In one embodiment, the reaction solvent is a mixture of dichloromethane and pyridine. In another embodiment, the reaction solvent is acetone. The UV absorbing polymers described herein are useful in applications where UV absorption is desired. For example, the polymer may be useful for combining with a suitable cosmetically acceptable carrier for cosmetic applications. The cosmetically-acceptable topical carrier is suitable for topical application to human skin and may include for example, one or more of vehicles such as water, ethanol, isopropanol, emollients, humectants, and/or one or more of surfactants/emulsifiers, fragrances, preservatives, waterproofing polymers, and similar ingredients commonly used in cosmetic formulations. As such, the UV absorbing polymer may be formulated using ingredients known in the art into a spray, lotion, gel, stick or other product forms. Similarly, according to certain embodiments, one may protect human skin from UV radiation by topically applying a composition comprising the UV absorbing polymer.

Furthermore, the UV absorbing polymers may be combined with other materials (e.g., plastics, rubber, or other solid materials) to reduce UV degradation of these materials (e.g., melt blending the material with the UV absorbing polymer or coating the material with the UV absorbing polymer). The incorporation of polymers of the present invention into such compositions may provide enhanced SPF (primarily UVB absorbance), enhanced PFA (primarily UVA absorbance), or enhancement of both.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Synthesis of a Di-Acid Monomer Containing a UV-Chromophore

FORMULA VI. SYNTHESIS OF DI-ACID CONTAINING MONOMER WITH PENDANT UV-CHROMOPHORE

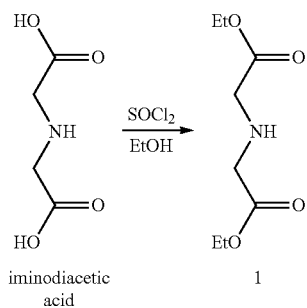

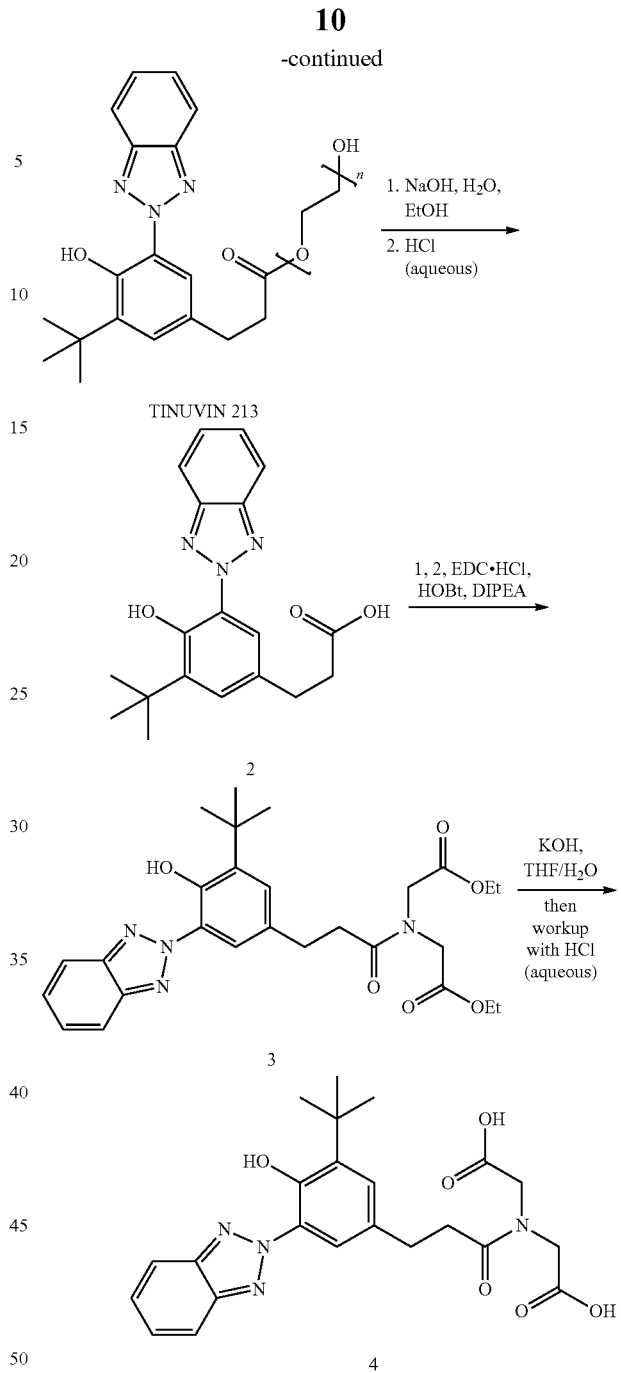

The synthesis of a di-acid monomer 4 containing a UV chromophore (2-{3-[3-(2H-1,2,3-benzotriazol-2-yl)-5-tert-butyl-4-hydroxyphenyl]-N-(carboxymethyl) propanamido}acetic acid) was performed as illustrated in FORMULA VI. Reactions were performed in oven-dried glassware. Solvents and reagents were purchased from commercial sources and were used as received, unless noted otherwise. NMR analysis was performed on a Varian Unity Inova 400 MHz spectrometer ($^1$H) spectrometer at 30° C.; chemical shifts are reported in parts per million (ppm) on the δ scale, and were referenced to residual protonated solvent peaks or tetramethylsilane. Spectra obtained in DMSO-$d_6$ were referenced to $(CHD_2)(CD_3)SO$ at $\delta_H$ 2.50.

Diethyliminodiacetate 1 was purchased from Aldrich or prepared using a procedure adapted from the literature (Kuehn, T.; Schwalbe, H. *J. Am. Chem. Soc.* 2000, 122, 6169). An oven-dried 2-neck round bottom flask containing a magnetic stir bar was fitted with a pressure equalizing addition funnel and reflux condenser with a nitrogen inlet adapter. Anhydrous ethanol (EtOH, 750 mL) was added to the flask; the flask was immersed in an ice-water bath. The addition funnel was charged with thionyl chloride ($SOCl_2$, 110 mL, 1503 mmol); $SOCl_2$ was added drop-wise to the EtOH with stirring. Once $SOCl_2$ addition was complete, iminodiacetic acid (50 g, 376 mmol) was added to the reaction mixture. The flask was transferred into a heated oil bath; the suspension was heated to reflux; the white suspension gradually became more translucent, ultimately becoming clear and colorless. The reaction mixture was refluxed overnight. The flask was removed from the oil bath, and the mixture was allowed to cool to room temperature. 2.5% aq. sodium bicarbonate ($NaHCO_3$, 200 mL) was added cautiously to the reaction mixture with vigorous stirring. Small portions of anhydrous $NaHCO_3$ were then added to the stirred mixture until gas evolution ceased. The mixture was vacuum filtered through paper and concentrated by rotary evaporation yielding an oil floating on a clear, aqueous solution. The biphasic mixture was transferred into a repartory funnel with 1:1 saturated aq. NaCl (brine)/$H_2O$ (200 mL). The aqueous layer was extracted with dichloromethane ($CH_2Cl_2$, 1×100 mL, then 2×50 mL). The $CH_2Cl_2$ layers were combined, washed with brine, dried over anhydrous $Na_2SO_4$, filtered through paper and concentrated by rotary evaporation to a pale tan oil. This oil was distilled under reduced pressure (~95° C. distillate at 0.65 torr) affording diethyliminodiacetate (1, 44.7 g) as a clear oil. $^1$H NMR (400 MHz, $CDCl_3$) δ ppm 4.20 (q, J=7.2 Hz, 4H), 3.46 (s, 4H), 2.04 (br. s., 1H), 1.28 (t, J=7.1 Hz, 6H).

The polyethylene glycol ester of 3-[3-(2H-1,2,3-benzotriazol-2-yl)-5-tert-butyl-4-hydroxyphenyl]propanoate (a UV-chromophore sold under the trade name TINUVIN 213 by BASF Corporation, Wyandotte, Mich.) (81.0 g) was added to a 2 L round bottom flask containing a magnetic stir bar. EtOH (600 mL) was added to the flask by funnel, and the mixture was stirred until homogeneous. Sodium hydroxide (NaOH, 30.8 g) was dissolved in $H_2O$ (400 mL); the basic solution was transferred into an addition funnel above the 2 L flask. The NaOH solution was added slowly to the stirred mixture; the pale amber cloudy solution immediately turned clear and dark orange. When addition was complete, the mixture was stirred overnight at room temperature. The solution was concentrated by rotary evaporation to remove most of the EtOH. The resulting orange oil was diluted to 1400 mL with $H_2O$. The mixture was stirred mechanically and was acidified to ~pH 1 by addition of 1 M aq. HCl (~700 mL). The resulting white precipitate was filtered and pressed to remove water, then recrystallized from EtOH. The first crop of crystals were long, thin colorless needles. The supernatant was removed and concentrated by rotary evaporation; a second crop of material was isolated as a white, amorphous solid. The two crops were combined and dried in a vacuum oven overnight affording 3-(3-(2H-benzo[d][1,2,3]triazol-2-yl)-5-(tert-butyl)-4-hydroxyphenyl) propanoic acid (2, 37.2 g) as a white solid. $^1$H NMR (400 MHz, DMSO-$d_6$) δ ppm 11.25 (br. s, 1H), 8.00-8.20 (m, 2H), 7.95 (d, J=2.1 Hz, 1H), 7.50-7.67 (m, 2H), 7.28 (d, J=2.1 Hz, 1H), 2.87 (t, J=7.5 Hz, 2H), 2.56 (t, J=7.5 Hz, 2H), 1.45 (s, 9H).

An oven-dried 1000 mL round bottom flask containing a magnetic stir bar was charged with 2 (35.00 g, 103.1 mmol) and 1 (23.42 g, 123.8 mmol). Anhydrous dimethylformamide (DMF, 344 mL) was added to the flask by cannula under nitrogen pressure; the resulting suspension was stirred vigorously until homogeneous. N-(3-Dimethylaminopropyl)-N'-ethylcarbodiimide hydrochloride (EDC.HCl, 23.72 g, 123.8 mmol) and hydroxybenzotriazole monohydrate (HOBt.$H_2O$, 3.16 g, 20.6 mmol) were added to the suspension. The suspension began to clear upon addition of the coupling reagent. Diisopropylethylamine (DIPEA, 18.0 mL, 103 mmol) was added slowly to the reaction mixture by syringe. The flask was sealed with a rubber stopper, and the mixture was stirred for 3 hours. After removing the magnetic stir bar, the mixture was concentrated by rotary evaporation, starting at 50° C. water bath temperature and increasing to 90° C. The resulting oil was transferred to a separatory funnel along with ethyl acetate (EtOAc, 550 mL) and 2.5% aq. $NaHCO_3$ (350 mL). The flask was shaken, and the layers were allowed to separate. The $NaHCO_3$ layer was back extracted with EtOAc (1×100 mL). The combined EtOAc layers were washed with 1M aq. HCl (2×200 mL) and brine (2×200 mL). The EtOAc layer was dried over anhydrous $Na_2SO_4$, filtered through paper and concentrated by rotary evaporation affording diethyl 2,2'-((3-(3-(2H-benzo[d][1,2,3]triazol-2-yl)-5-(tert-butyl)-4-hydroxyphenyl)propanoyl)azanediyl)diacetate (3, 52.23 g) as a yellow oil that was used without further purification. On standing, the oil solidified into stellate off-white crystals. $^1$H NMR (400 MHz, $CDCl_3$) δ ppm 11.78 (s, 1H), 8.13 (d, J=2.1 Hz, 1H), 7.89-7.96 (m, 2H), 7.43-7.51 (m, 2H), 7.22 (d, J=2.1 Hz, 1H), 4.14-4.27 (m, 8H), 2.98-3.07 (m, 2H), 2.62-2.73 (m, 2H), 1.50 (s, 9H), 1.17-1.33 (m, 6H).

Tetrahydrofuran (THF, 800 mL) was transferred into a 1000 mL round bottom flask containing 3 (52.23 g, 103.1 mmol theoretical from previous reaction) and a magnetic stir bar. The mixture was stirred until 3 was fully dissolved. Water (200 mL) was then added to the flask. Lithium hydroxide (12.34 g, 515.7 mmol) was added slowly to the stirred reaction mixture; the clear, pale yellow reaction mixture immediately turned orange. After stirring the mixture overnight, the solution was concentrated to a volume of ~300 mL by rotary evaporation to remove the majority of THF. The resulting dark orange solution was transferred to a 2 L separatory funnel with an additional 1300 mL of $H_2O$. The aqueous solution was extracted with diisopropyl ether (1×250 mL); the ether layer was back-extracted with water (1×200 mL). The combined aqueous layers were transferred into a 4 L Erlenmeyer flask. With vigorous mechanical stirring, the solution was acidified to ~pH 1 with 1M aq. HCl (~750 mL); this generated a white precipitate. EtOAc was added to the stirred suspension until all of the precipitate had dissolved (final volume of EtOAc added was 750 mL). The organic and aqueous layers were separated; the aqueous layer was extracted with an additional portion of EtOAc (1×200 mL). The EtOAc layers were combined, dried over anhydrous $Na_2SO_4$, filtered through paper, and concentrated by rotary evaporation affording a white paste. The paste was triturated with 2:3 EtOAc/hexanes (500 mL). The precipitate was filtered, then dried in a vacuum oven affording 2,2'-((3-(3-(2H-benzo[d][1,2,3]triazol-2-yl)-5-(tert-butyl)-4-hydroxyphenyl)propanoyl)azanediyl)diacetic acid (4, 32.04 g) as a fine white solid. $^1$H NMR (400 MHz, DMSO-$d_6$) δ ppm 11.91-13.25 (br s, 1H), 11.24 (s, 1H), 8.03-8.12 (m, 2H), 7.96 (d, J=2.1 Hz, 1H), 7.55-7.63 (m, 2H), 7.28 (d, J=2.0 Hz, 1H), 4.21 (s, 2H), 3.99 (s, 2H), 2.85 (t, J=6.8 Hz, 2H), 2.63 (t, J=7.5 Hz, 2H), 1.46 (s, 9H).

Example 2

Synthesis of a Di-Acid Monomer Containing an Oil-Solubilizing Moiety

FORMULA VII. SYNTHESIS OF 6,
A SOLUBILIZING DI-ACID MONOMER

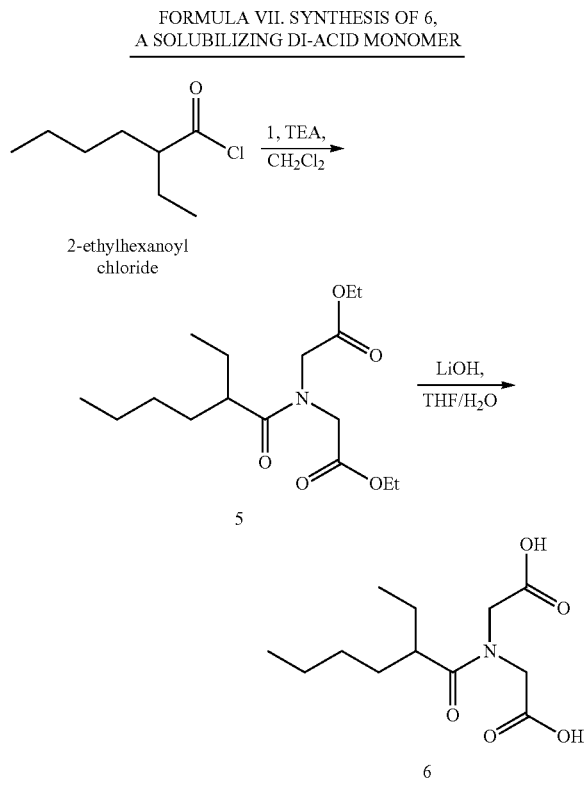

Synthesis of a di-acid monomer containing an oil-solubilizing moiety was prepared as illustrated in FORMULA VII. Diethyliminodiacetate (1, 13.42 g, 70.93 mmol) was added by syringe to an oven-dried 500 mL round bottom flask fitted with a rubber septum and containing a magnetic stir bar. Anhydrous $CH_2Cl_2$ (200 mL) was added to the flask by cannula under nitrogen pressure. Triethylamine (TEA, 8.2 mL, 59 mmol) was added to the flask by syringe. 2-Ethylhexanoyl chloride was then added slowly to the stirred reaction mixture by syringe. The mixture was stirred for 20 hours, during which time a white precipitate evolved. The reaction mixture was concentrated by rotary evaporation; the resulting oil was diluted with EtOAc (250 mL) and transferred to a separatory funnel. The EtOAc solution was washed with 1M aq. HCl (2×100 mL) then with brine (1×250 mL). The EtOAc layer was dried over anhydrous $Na_2SO_4$, filtered through paper, and concentrated by rotary evaporation affording diethyl 2,2'-((2-ethylhexanoyl)azanediyl)diacetate (5, 19.45 g) as a colorless oil that was used in subsequent reactions without further purification. $^1H$ NMR (400 MHz, $CDCl_3$) δ ppm 4.08-4.29 (m, 8H), 2.44 (tt, J=8.1, 5.4 Hz, 1H), 1.56-1.75 (m, 2H), 1.36-1.55 (m, 2H), 1.14-1.35 (m, 10H), 0.79-0.94 (m, 6H).

THF (500 mL) was transferred into the 1 L round bottom flask containing crude 5 (19.5 g, 59.1 mmol; theoretical yield from previous reaction) and a magnetic stir bar by cannula under nitrogen pressure. The mixture was stirred until 5 was fully dissolved. Water (100 mL) was added to the mixture, followed by lithium hydroxide (7.1 g, 296 mmol); the solution turned cloudy and pale green. The mixture was stirred overnight at room temperature. The reaction mixture was concentrated by rotary evaporation to a pale yellow syrup. This was diluted with water (500 mL), transferred to a separatory funnel and washed with diisopropyl ether (1×150 mL). The ether layer was back-extracted with water (1×100 mL) then acidified to ~pH 1 with 1M aq. HCl. The acidified aqueous layer was then extracted with EtOAc (3×100 mL). The organic layers were combined, dried over anhydrous $Na_2SO_4$, filtered through paper, and concentrated by rotary evaporation to a clear oil. The oil was triturated in hexanes to remove residual EtOAc. The hexane was decanted, leaving a semi-solid that was heated at 80° C. in a vacuum oven overnight. This afforded the desired product 2,2'-((2-ethylhexanoyl)azanediyl)diacetic acid (6, 11.01 g) as a white, crystalline solid. $^1H$ NMR (400 MHz, DMSO-$d_6$) δ ppm 11.31-13.50 (m, 1H), 4.19 (dd, J=31.4, 18.6 Hz, 2H), 3.97 (dd, J=33.5, 17.9 Hz, 2H), 2.41-2.48 (m, 1H), 1.40-1.55 (m, 2H), 1.33-1.40 (m, 1H), 1.25-1.33 (m, 1H), 1.07-1.25 (m, 4H), 0.68-0.93 (m, 6H).

Example 3

Polymerization of Monomer 4 with Glyceryl Monostearate

A round bottom flask containing a magnetic stir bar was charged with monomer 4 (3.80 g, 8.37 mmol) and glyceryl monostearate (a monoglyceride sold under the trade name MYVEROL 18-06 by Kerry Group plc, Kerry, Ireland; purified by recrystallization from EtOAc; 3.00 g, 8.37 mmol). The flask was fitted with a vacuum distillation head; the air in the flask was evacuated under vacuum (0.2 to 1 torr) for 1 hour. The flask was then backfilled with nitrogen. The distillation head was removed, and esterification catalyst tin (II) 2-ethylhexanoate (27 µL, 0.08 mmol) was added to flask by syringe. The apparatus was reassembled and subjected to 3 cycles of vacuum purges followed by nitrogen backfills. After the final nitrogen fill, the reaction flask was immersed in an oil bath which pre-heated to 180° C. The mixture was stirred under nitrogen for 4 hours, then allowed to cool to room temperature under nitrogen atmosphere. The polymer was removed from the reaction vessel by freezing the flask in liquid nitrogen, then fracturing the polymer into smaller pieces; the material was then transferred into a storage container. The container was allowed to warm to room temperature under vacuum. This afforded the polymer as a pale yellow solid (4.73 g). $^1H$ NMR (400 MHz, $CDCl_3$) δ ppm 11.51-11.90 (1H), 7.97-8.25 (1H), 7.67-7.97 (2H), 7.31-7.60 (2H), 7.06-7.25 (1H), 4.95-5.56 (1H), 4.15 (8H), 2.80-3.14 (2H), 2.47-2.80 (2H), 2.17 (2H), 1.48 (11H), 1.24 (28H), 0.87 (3H). Due to the broadness of the proton resonances of the polymer $^1H$ spectra, integrals are rounded to the nearest integer value.

Gel permeation chromatography for molecular weight determination was performed at 35° C. on a Waters Alliance 2695 Separations Module (Waters, Milford, Mass.) at a flow rate of 0.5 mL/min THF (stabilized w/0.025% BHT). The 2695 was equipped with two GPC columns in series (Waters Corp HR 0.5 and HR3) with dimensions of 7.8×300 mm with 5 µm particle size) and a Waters model 410 refractive index detector. The molecular weights of the samples were determined by comparison to polystyrene standards. Standards were prepared by weighing 1-2 mg of each polystyrene (PS) polymer into a 2 mL vial with THF solvent (2 standards per vial); samples were filtered (0.22 µm) prior to analysis. Polystyrene standards spanned a range between 70,000 to 600 Daltons, and were manufactured by three vendors (Polymer Standards Service-USA, Phenomenex and Shodex). The resultant calibration curve provided an $r^2$=0.9999. Experimental samples were dissolved in THF at a concentration of 3-5 mg/mL and filtered (0.22 μm) prior to analysis. Number average molecular weight ($M_n$) and weight average molecular weight ($M_w$) are reported for each material. GPC (THF) analysis for the polymer of Example 3: $M_n$ 5078, $M_w$ 10202.

HPLC analysis was used to determine residual monomer bearing UV-chromophore (e.g., 4) following polymerization; results are reported as weight % residual monomer. This technique used an external standard of the appropriate monomer. The standard solution was prepared by weighing 1-2 mg (±0.1 mg) of the monomer into a 10 mL volumetric flask. The material was dissolved in methanol (MeOH) and diluted to the mark. 8-10 mg of polymer sample was dissolved in 1.0 mL of THF in a 4 mL vial and then dissolved by sonication. After dissolution, 2.0 mL of MeOH was added with agitation. The cloudy solution was then filtered through a 0.2 um syringe filter into an HPLC vial. HPLC analysis was performed at 50° C. on an Agilent 1100 HPLC with a Discovery $C_{18}$ column (150×4.6 mm, 3 μm particle size) and photodiode array detector at 302 nm (Agilent Technologies, Santa Clara, Calif.). The gradient was 40:60 to 10:90 AB over 5.5 minutes, where A=water with 0.1% trifluoroacetic acid, B=acetonitrile, with total runtime of 6.5 minutes. HPLC analysis for the polymer of Example 3: 0.16 wt. % residual 4.

Sun protection factor (SPF) measurements for UV absorbing polymers were performed using the following in vitro sun protection test method. Polymer samples were measured into 8 mL glass vials. Mixed $C_{12}$ to $C_{15}$ alkyl benzoates (a cosmetic oil solvent sold under the trade name FINSOLV TN by Innospec, Newark, N.J.) was added to the vial to achieve the desired weight percent solution of polymer. A magnetic stir bar was added to the vial, which was then sealed with a Teflon lined screw cap. The polymer/oil solution was stirred in a 100° C. aluminum reaction block until homogeneous. Once cooled, 32 mg of polymer solution was applied to a poly(methyl methacrylate) (PMMA) plate (a test substrate sold under the trade name HELIOPLATE HD6 by Helioscience, Marseille, France). The solution was spread evenly over the plate using one finger using a latex cot until the weight of sample on the plate had decreased to 26 mg. The baseline transmission was measured using an HD6 plate as received from the manufacturer. Absorbance was measured using a calibrated Labsphere UV-1000S UV transmission analyzer (Labsphere, North Sutton, N.H., USA). The absorbance measures were used to calculate SPF indices. SPF was calculated using methods known in the art. The equation used for calculation of SPF is described by Equation 1.

$$SPF_{in\ vitro} = [\int E(\lambda)I(\lambda)d\lambda]/[\int E(\lambda)I(\lambda)10^{-A_0(\lambda)}(d\lambda)] \quad (1)$$

where:
$E(\lambda)$=Erythema action spectrum
$I(\lambda)$=spectral irradiance received from the UV source
$A_0(\lambda)$=mean monochromatic absorbance of the test product layer before UV exposure
$d\lambda$=Wavelength step (1 nm)

and the integrations are each performed over the wavelength range from 290 nm to 400 nm.

Results of in vitro SPF testing are reported as [wt. % in FINSOLV TN, mean SPF value]. Analytical data for the polymer of Example 3 follows: SPF testing: [50%, 17.5], [40%, 12.7], [30%, 11.3], [20%, 10.7], [10%, 6.0]. A summary of the in vitro SPF results for all polymers is provided in Table 1 within Example 26.

Example 4

Polymerization of Monomer 4 with Glyceryl Monolaurate

Monomer 4 (3.00 g, 6.60 mmol), glyceryl monolaurate (a monoglyceride sold under the trade name MONOMULS 90-L 12 by Cognis Corporation, Monheim, Germany; 1.81 g, 6.60 mmol) and tin (II) 2-ethylhexanoate (21 μL, 0.07 mmol) were reacted as described in Example 3 affording a yellow solid (3.85 g). HPLC analysis: 0.03 wt. % residual 4. GPC (THF): $M_n$ 3500, $M_w$ 9600. $^1$H NMR (400 MHz, CDCl$_3$) δ ppm 11.47-12.05 (1H), 7.97-8.24 (1H), 7.61-7.97 (2H), 7.28-7.61 (2H), 7.21 (1H), 5.27 (1H), 3.70-4.74 (8H), 2.80-3.16 (2H), 2.46-2.80 (2H), 1.87-2.45 (2H), 1.35-1.77 (11H), 1.24 (18H), 0.87 (3H). SPF testing: [29%, 19.3], [40%, 29.0].

Example 5

Polymerization of Monomer 4 with Glyceryl Monooleate

Monomer 4 (3.00 g, 6.60 mmol), glyceryl monooleate (a monoglyceride sold under the trade name MONOMULS 90-O 18 by Cognis Corporation, Monheim, Germany; 2.35 g, 6.60 mmol) and tin (II) 2-ethylhexanoate (21 μL, 0.07 mmol) were reacted as described in Example 3 affording a dark yellow hard gum (4.55 g). HPLC analysis: 0.05 wt. % residual 4. GPC (THF): $M_n$ 3115, $M_w$ 4148. $^1$H NMR (400 MHz, CDCl$_3$) δ ppm 11.80 (1H), 7.99-8.31 (1H), 7.68-7.97 (2H), 7.31-7.59 (2H), 7.03-7.24 (1H), 4.84-5.62 (4H), 3.55-4.77 (8H), 2.83-3.11 (2H), 2.49-2.83 (4H), 2.11-2.48 (2H), 2.03 (4H), 1.39-1.70 (11H), 0.99-1.38 (18H), 0.72-0.99 (3H). SPF testing: [19%, 16.0], [38%, 22.7].

Example 6

Polymerization of Monomer 4 and Sebacic Acid with Glyceryl Monostearate

Monomer 4 (1.90 g, 4.28 mmol), sebacic acid (0.85 g, 4.18 mmol), glyceryl monostearate (MYVEROL 18-06; 3.00 g, 8.37 mmol), and tin (II) 2-ethylhexanoate (27 μL, 0.08 mmol) were reacted as described in Example 3 affording a waxy, pale yellow solid (4.55 g). HPLC analysis: 0.02 wt. % residual 4. GPC (THF): $M_n$ 3300, $M_w$ 9500. $^1$H NMR (400 MHz, CDCl$_3$) δ ppm 11.03-12.14 (1H), 7.99-8.26 (1H), 7.69-7.97 (2H), 7.32-7.62 (2H), 7.02-7.25 (1H), 4.80-5.50 (2H), 3.75-4.74 (12H), 2.83-3.26 (2H), 2.47-2.83 (2H), 1.93-2.43 (8H), 1.40-1.77 (17H), 1.25 (64H), 0.69-0.95 (6H). SPF testing: [20%, 10.4].

Example 7

Polymerization of Monomer 4 and Succinic Acid with Glyceryl Monostearate

Monomer 4 (1.90 g, 4.18 mmol), succinic acid (0.49 g, 4.18 mmol), glyceryl monostearate (MYVEROL 18-06; 3.00 g, 8.37 mmol) and tin (II) 2-ethylhexanoate (21 μL, 0.07 mmol) were reacted as described in Example 3 affording a pale yellow solid (4.51 g). HPLC analysis: 0.02 wt. % residual 4. GPC (THF): $M_n$ 3,300, $M_w$ 9,100. $^1$H NMR (400

MHz, CDCl$_3$) δ ppm 11.46-11.99 (1H), 8.01-8.27 (1H), 7.72-7.99 (2H), 7.30-7.63 (2H), 7.08-7.25 (1H), 4.82-5.66 (2H), 3.50-4.73 (12H), 2.84-3.40 (2H), 2.45-2.83 (5H), 2.03-2.43 (5H), 1.40-1.87 (m, 13H), 1.27 (56H), 0.74-0.97 (6H). SPF testing: [20%, 10.6], [40%, 15.0].

Example 8

Polymerization of Monomers 4 and 6 with Glyceryl Monostearate

Monomer 4 (3.00 g, 6.60 mmol), ethyl hexyl iminodiacetate 6 (1.71 g, 6.60 mmol), glyceryl monostearate (MYVEROL 18-06; 4.73 g, 13.2 mmol) and tin (II) 2-ethylhexanoate (21 μL, 0.07 mmol) were reacted as described in Example 3 affording a pale yellow opaque solid (8.15 g). HPLC analysis: 0.01 wt. % residual 4. GPC (THF): M$_n$ 4200, M$_w$ 11800. $^1$H NMR (400 MHz, CDCl$_3$) δ ppm 11.43-12.03 (1H), 8.01-8.32 (1H), 7.70-7.99 (2H), 7.31-7.58 (2H), 7.05-7.26 (1H), 4.95-5.52 (2H), 3.38-4.69 (15H), 2.84-3.23 (2H), 2.52-2.81 (2H), 1.96-2.52 (5H), 1.36-1.78 (17H), 1.26 (60H), 0.61-0.96 (9H). SPF testing: [10%, 5], [21%, 11], [29%, 14], [40%, 17].

Example 9

Polymerization of Monomer 4 and Maleic Acid with Glycerol Monooleate

Monomer 4 (2.00 g, 4.40 mmol), maleic acid (0.51 g, 4.40 mmol), glyceryl monooleate (MONOMULS 90-O 18; 3.14 g, 8.80 mmol) and tin (II) 2-ethylhexanoate (14 μL, 0.04 mmol) were reacted as described in Example 3 affording a clear, orange-yellow solid (4.01 g). HPLC analysis: <0.01 wt. % residual 4. GPC (THF): M$_n$ 3044, M$_w$ 8628. $^1$H NMR (400 MHz, CDCl$_3$) δ ppm 11.49-11.95, 8.00-8.24, 7.70-7.96, 7.46, 7.22, 5.27, 3.71-4.72, 2.45-3.16, 2.11-2.42, 2.04, 1.37-1.69, 1.24, 0.71-0.93. SPF testing: [20%, 13.7], [29%, 11.7], [34%, 14.7].

Example 10

Polymerization of Monomer 4 and Maleic Acid with Glycerol Monostearate

Monomer 4 (2.00 g, 4.40 mmol), maleic acid (510 mg, 4.40 mmol), glyceryl monostearate (MYVEROL 18-06; 3.16 g, 8.80 mmol) and tin (II) 2-ethylhexanoate (29 μL, 0.09 mmol) were reacted as described in Example 3, then under reduced pressure for an additional hour at 180° C. affording an opaque yellow-orange solid (4.59 g). HPLC analysis: <0.01 wt. % residual 4. GPC (THF): M$_n$ 3205, M$_w$ 8605. $^1$H NMR (400 MHz, CDCl$_3$) δ ppm 11.47-11.99 (1H), 7.97-8.26 (1H), 7.70-7.97 (2H), 7.33-7.62 (2H), 7.10-7.24 (1H), 6.56-6.94 (1H), 4.84-5.50 (1H), 3.87-4.67 (12H), 2.83-3.15 (2H), 2.48-2.83 (2H), 2.32 (4H), 1.37-1.70 (15H), 1.26 (57H), 0.70-0.95 (6H). SPF testing: [25%, 15], [35%, 20], [40%, 44].

Example 11

Polymerization of Monomer 4 and Itaconic Acid with Glycerol Monostearate

Monomer 4 (2.50 g, 5.50 mmol), itaconic acid (715 mg, 5.50 mmol), glyceryl monostearate (MYVEROL 18-06; 3.94 g, 11.00 mmol) and tin (II) 2-ethylhexanoate (38 μL, 0.11 mmol) were reacted as described in Example 3 affording a pale orange opaque solid (5.92 g). HPLC analysis: 0.01 wt. % residual 4. GPC (THF): M$_n$ 2498, M$_w$ 4543. $^1$H NMR (400 MHz, CDCl$_3$) δ ppm 11.54-12.06 (1H), 7.99-8.23 (1H), 7.68-7.97 (2H), 7.32-7.58 (2H), 7.06-7.25 (1H), 6.00-6.49 (1H), 5.55-5.87 (1H), 4.80-5.46 (1H), 3.97-4.70 (11H), 3.53-3.87 (1H), 3.14-3.49 (1H), 2.82-3.11 (2H), 2.55-2.82 (2H), 2.09-2.45 (5H), 1.39-1.75 (14H), 1.26 (58H), 0.76-0.96 (6H). SPF testing: [10%, 6], [20%, 9], [40%, 22].

Example 12

Polymerization of Monomer 4 with Glycerol Monolaurate and 1 k Silicone

Monomer 4 (2.02 g, 4.44 mmol), glycerol monolaurate (MONOMULS 90-L 12; 974 mg, 3.55 mmol), monodicarbinol polydimethylsiloxane (a carbinol modified polydimethylsiloxane obtained from Gelest, Morrisville, Pa.; catalog number MCR-C61, ~1000 M.W., 903 mg, ~0.88 mmol) and tin (II) 2-ethylhexanoate (7 μL, 0.02 mmol) were reacted as described in Example 3, with a reaction time of 5 hours (instead of 4 hours) affording a pale yellow, clear, brittle solid (3.10 g). HPLC analysis: 0.16 wt. % residual 4. GPC (THF): M$_n$ 4100, M$_w$ 11,900. $^1$H NMR (400 MHz, CDCl$_3$) δ ppm 11.52-11.91 (1H), 7.97-8.22 (1H), 7.93 (2H), 7.48 (2H), 7.04-7.26 (1H), 4.96-5.49 (1H), 3.81-4.70 (12H), 3.11-3.44 (1H), 2.81-3.10 (3H), 2.48-2.81 (3H), 2.07-2.45 (3H), 1.49 (18H), 0.98-1.37 (21H), 0.66-0.98 (5H), 0.28-0.61 (1H), 0.00-0.15 (22H). SPF testing: [40%, 22], [75%, 155].

Example 13

Polymerization of Monomer 4 with Glycerol Monolaurate and 5 k Silicone

Monomer 4 (6.00 g, 13.2 mmol), glycerol monolaurate (MONOMULS 90-L 12; 3.53 g, 12.89 mmol), hydroxy terminated polydimethylsiloxane (a carbinol modified polydimethylsiloxane obtained from Gelest, Morrisville, Pa.; catalog DMS-C21, ~5000 M.W., 1.65 g, ~0.33 mmol) and tin (II) ethylhexanoate (21 μL, 0.07 mmol) were reacted as described in Example 3 with a reaction time of 7 hours (instead of 4 hours) affording an opaque yellow solid (10.10 g). HPLC analysis: 0.04 wt. % residual 4. GPC (THF): M$_n$ 3600, M$_w$ 11700. $^1$H NMR (400 MHz, CDCl$_3$) δ ppm 11.31-11.97, 7.98-8.21, 7.87, 7.43, 6.88-7.25, 5.02-5.53, 3.82-4.71, 3.63-3.78, 3.50-3.59, 3.35-3.49, 2.99, 2.49-2.82, 1.97-2.44, 1.71-1.92, 1.37-1.68, 1.25, 0.87, 0.03-0.15. SPF testing: [63%, 76].

Example 14

Polymerization of Monomer 4 with Glycerol Monolaurate and <1 k Silicone

Monomer 4 (6.00 g, 13.2 mmol), glycerol monolaurate (MONOMULS 90-L 12; 3.26 g, 11.9 mmol), hydroxy terminated polydimethylsiloxane (a carbinol modified polydimethylsiloxane obtained from Gelest, Morrisville, Pa. Gelest DMS-C16, ~725 M.W., 0.96 g, ~1.32 mmol) and tin (II) ethylhexanoate (21 μL, 0.07 mmol) were reacted as described in Example 3 affording a pale yellow, semi-transparent solid (8.43 g). HPLC analysis: 0.21 wt. % residual 4. GPC (THF): M$_n$ 3300, M$_w$ 9200. $^1$H NMR (400 MHz, CDCl$_3$) δppm 11.14-12.07 (1H), 7.99-8.29 (1H), 7.63-7.96 (2H), 7.31-7.57 (2H), 7.06-7.25 (1H), 4.96-5.43 (1H), 3.67-4.71 (12H), 2.83-3.13 (3H), 2.45-2.83 (3H), 2.00-2.43 (3H), 1.35-1.85 (20H), 1.24 (23H), 0.74-1.01 (4H), 0.40-0.67 (1H), −0.01-0.18 (33H). SPF testing: [58%, 118]; [40%, 16].

Example 15

Polymerization of Monomer 4 with Glycerol Monolaurate and Dodecanediol

Monomer 4 (6.00 g, 13.2 mmol), glycerol monolaurate (MONOMULS 90-L 12; 3.26 g, 11.9 mmol), 1,12-dodecanediol (267 mg, 1.32 mmol) and tin (II) ethylhexanoate (21 μL, 0.07 mmol) were reacted as described in Example 3, with a reaction time of 6 hours (instead of 4 hours) affording a transparent yellow solid (8.39 g). HPLC analysis: 0.02 wt. % residual 4. GPC (THF): $M_n$ 3600, $M_w$ 9800. $^1$H NMR (400 MHz, CDCl$_3$) δ ppm 11.53-11.90 (1H), 7.97-8.26 (1H), 7.59-7.97 (2H), 7.46 (2H), 7.22 (1H), 5.27 (1H), 3.70-4.73 (7H), 2.83-3.16 (2H), 2.43-2.81 (2H), 2.11-2.40 (3H), 2.04 (1H), 1.79 (1H), 1.36-1.66 (14H), 1.24 (20H), 0.66-0.98 (4H).

Example 16

Polymerization of Monomer 4 with Glycerol Monolaurate and Triglycerol Monostearate Monomer 4 (6.00 g, 13.2 mmol), glycerol monolaurate (MONOMULS 90-L 12; 3.26 g, 11.9 mmol), triglycerol monostearate (a polyglycerol derivative sold under the trade name TGMS-KFG by Lonza, Allendale, N.J.; 0.335 g, 0.66 mmol) and tin (II) ethylhexanoate (21 μL, 0.07 mmol) were reacted as described in Example 3 with a reaction time of 6 hours (instead of 4 hours) affording a transparent yellow solid (7.53 g). HPLC analysis: 0.08 wt. % residual 4. GPC (THF) $M_n$ 3500, $M_w$ 11600. $^1$H NMR (400 MHz, CDCl$_3$) δ ppm 11.48-11.99 (2H), 7.98-8.22 (2H), 7.68-7.98 (4H), 7.29-7.54 (4H), 7.22 (2H), 5.28 (2H), 3.79-4.81 (17H), 2.81-3.16 (5H), 2.50-2.81 (4H), 1.99-2.45 (4H), 1.36-1.74 (23H), 1.25 (34H), 0.88 (6H).

Example 17

Synthesis of a Tri-Acid Monomer Containing a UV-Chromophore

FORMULA VIII. HYDROLYSIS REACTION TO GENERATE TRI-ACID FUNCTIONAL MONOMER

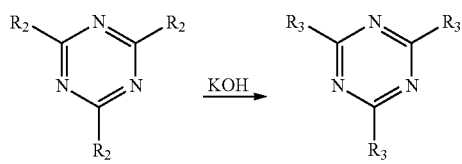

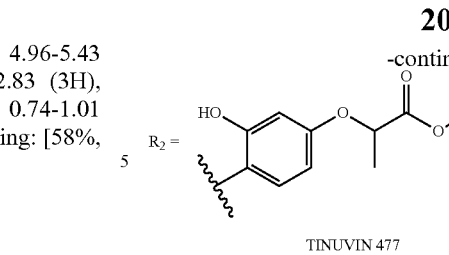

TINUVIN 477

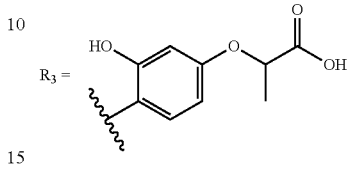

7

The synthesis of tri-acid monomer 7 is illustrated in FORMULA VIII. Trioctyl 2,2',2"-(((1,3,5-triazine-2,4,6-triyl)tris(3-hydroxybenzene-4,1-diyl))tris(oxy))tripropanoate (a UV-chromophore sold under the trade name TINUVIN 477 by BASF Corporation, Wyandotte, Mich.; material number 55430622, 42.4 g) was transferred into a 500 mL round bottom flask containing a magnetic stir bar. MeOH (300 mL) was added to the flask; stirring the mixture generated a yellow suspension. Water (50 mL) was added to the flask, and the suspension changed from yellow to white. Potassium hydroxide pellets (33.1 g) were added slowly to the stirred suspension, causing an immediate color change to yellow; further addition of KOH produced a dark orange color. The reaction mixture was stirred for 20 hours at room temperature and then concentrated by rotary evaporation to remove the majority of MeOH. The resulting dark orange solution was diluted to 600 mL with water and transferred into a reparatory funnel. The aqueous solution was washed with diisopropyl ether (2×125 mL) and then acidified to ~pH 1 with the addition of 6 M aq. HCl, causing the formation of a precipitate. The aqueous layer was extracted with EtOAc (1×300 mL, 1×100 mL then 1×50 mL). The EtOAc layers were combined, washed with brine, dried over Na$_2$SO$_4$ and filtered through a fluted paper cone. The solution was concentrated by rotary evaporation affording a yellow paste; the paste was triturated with hexanes (~400 mL), and the resulting suspension was filtered. The filtered solids were dried under vacuum at ~80° C., affording the desired product as a yellow solid (22.4 g). $^1$H NMR (400 MHz, DMSO-d$_6$) δ ppm 13.27 (s, 1H), 13.10 (br. s., 3H), 12.79 (br. s., 2H), 7.98-8.48 (3H), 6.26-6.81 (6H), 4.84-5.20 (3H), 1.46-1.67 (9H).

Example 18

Polymerization of Monomer 7 with Glyceryl Monostearate (1:1.5 Ratio)

Solution polymerizations of compound 7 were performed using a variation of a literature procedure (Moore, J. S.; Stupp, S. I. *Macromolecules* 1990, 23, 65-70.) Monomer 7 (1.00 g, 1.61 mmol), glycerol monostearate (MYVEROL 18-06, 865 mg, 2.41 mmol) and catalyst 4-dimethylamino pyridine/p-toluene sulfonic acid 1:1 salt (DPTS; 284 mg, 0.97 mmol) were added to an oven-dried 100 mL round bottom flask containing a magnetic stir bar. The flask was sealed with a rubber septum and flushed with nitrogen gas Anhydrous CH$_2$Cl$_2$ (40 mL) was introduced into the flask by syringe; the resulting suspension was stirred whilst warming in an oil bath at 50° C. Pyridine (3 mL) was then added to the flask with stirring, causing most of the suspended solids to dissolve in the solution. The flask was then removed from the oil bath and allowed to cool to room temperature. Diisopropylcarbodiimide (1.24 mL, 8.04 mmol) was added to the stirred solution by syringe. The solution briefly became clear, and then a precipitate formed. The reaction mixture was stirred for 26 hours and then poured into MeOH generating a yellowish precipitate. The precipitate was filtered from the suspension and dried in a vacuum oven at ~50° C. affording the polymer as a white powder with slight yellow cast (1.57 g). GPC (THF): $M_n$ 11,200, $M_w$ 21,700. $^1$H NMR (400 MHz, CDCl$_3$) δ ppm 11.83-13.82 (3H), 7.32-9.02 (4H), 5.68-7.15 (9H), 5.12-5.68 (2H), 3.45-5.12 (17H), 2.00-2.71 (6H), 1.42-2.00 (26H), 0.95-1.42 (92H), 0.87 (10H). SPF testing: [20%, 23].

Example 19

Polymerization of Monomer 7 with Glyceryl Monolaurate (1:1 Ratio)

Monomer 7 (1.00 g, 1.61 mmol), glyceryl monolaurate (MONOMULS 90-L 12; 441 mg, 1.61 mmol), and DPTS catalyst (284 mg, 0.97 mmol) were added to an oven-dried 100 mL round bottom flask containing a magnetic stir bar. The flask was sealed with a rubber septum and flushed with nitrogen. Pyridine (6 mL) was added to the flask by syringe, followed by CH$_2$Cl$_2$ (30 mL). With stirring, the reaction mixture became a slightly cloudy solution. While stirring the mixture at room temperature, diisopropylcarbodiimide (1.25 mL, 8.04 mmol) was added to the reaction mixture. The flask was immersed in an oil bath at 50° C. which was gradually cooled to 35° C. The mixture was stirred under nitrogen at 35° C. for 26 hours, then poured into 300 mL of vigorously stirred MeOH. The volume of the suspension was adjusted to 500 mL with additional MeOH; the solid was isolated by vacuum filtration and then dried overnight in a vacuum oven at ~50° C. The resulting polymer was a pale yellow solid (1.20 g). GPC (THF): $M_n$ 19,100, $M_w$ 45,233. $^1$H NMR (400 MHz, CDCl$_3$) δ ppm 12.05-13.64 (m, 1H), 7.46-8.95 (3H), 5.83-7.20 (6H), 2.94-5.83 (12H), 1.98-2.69 (5H), 1.54 (21H), 0.95-1.41 (37H), 0.85 (7H).

Example 20

Polymerization of Monomer 7 with Glycerol Monolaurate (1:1.5 Ratio)

Monomer 7 (1.00 g, 1.61 mmol), glyceryl monolaurate (MONOMULS 90-L 12, 662 mg, 2.41 mmol) and DPTS catalyst (284 mg, 0.97 mmol) were added to an oven-dried 100 mL round bottom flask containing a magnetic stir bar. The flask was sealed with a rubber septum, flushed with nitrogen, and immersed into a 50° C. oil bath. Pyridine (6 mL) and anhydrous CH$_2$Cl$_2$ (40 mL) were added to the flask by syringe. The flask was then removed from the oil bath and allowed to cool to room temperature. Diisopropylcarbodiimide (1.25 mL, 8.04 mmol) was then added to the stirred reaction mixture by syringe. The mixture was stirred for 21 hours and then poured into vigorously stirred MeOH (300 mL). The volume of the suspension was adjusted to 500 mL with MeOH; the precipitate was isolated by vacuum filtration and dried overnight in a vacuum oven at ~50° C. The resulting polymer was a pale yellow solid (1.19 g). GPC (THF): $M_n$ 9,957, $M_w$ 18,661. $^1$H NMR (400 MHz, CDCl$_3$) δ ppm 12.08-13.78 (2H), 7.33-9.29 (3H), 5.83-6.95 (2H), 3.16-5.74 (6H), 1.99-2.68 (2H), 1.54 (9H), 1.24 (13H), 0.71-0.98 (3H). SPF testing: [39%, >500].

Example 21

Polymerization of Monomer 7 with Glycerol Monostearate (1:1 Ratio)

Monomer 7 (1.00 g, 1.61 mmol), glyceryl monostearate (MYVEROL 18-06; 577 mg, 1.61 mmol) and DPTS catalyst (284 mg) were added to a 100 mL oven-dried round bottom flask containing a magnetic stir bar. The flask was fitted with a rubber septum, flushed with nitrogen, and immersed in a 50° C. oil bath Anhydrous CH$_2$Cl$_2$ (40 mL) was added by syringe, followed by pyridine (6 mL); with stirring, most solids dissolved in the solvent, forming a clear solution. The flask was removed from the oil bath and the mixture was allowed to cool to room temperature. Diisopropylcarbodiimide was added to the stirred reaction mixture by syringe. The mixture was stirred for 25 hours, then poured into vigorously stirred MeOH (500 mL). The resulting precipitate was collected by vacuum filtration and dried overnight in a vacuum oven at ~50° C. The resulting polymer was a cream-colored solid (1.34 g). HPLC analysis: 0.01 wt. % residual monomer 7. GPC (THF): $M_n$ 13,036, $M_w$ 24,948. $^1$H NMR (400 MHz, CDCl$_3$) δ ppm 11.53-13.89 (3H), 7.40-9.02 (4H), 5.71-7.23 (9H), 3.54-5.58 (7H), 2.06-2.58 (5H), 1.00-2.03 (108H), 0.88 (10H).

Example 22

Polymerization of Monomer 7 with Glyceryl Monolaurate Under Melt Conditions

Triacid monomer 7 (3.51 g), adipic acid (1.15 g), glycerol monolaurate (MONOMULS 90-L 12; 3.48 g), and stearyl alcohol (2.86 g) were weighed into a 100 mL 2-neck round bottom flask. The flask was equipped with a nitrogen inlet on the side neck and a distillation adapter on the center neck leading to an ice chilled receiving flask. A magnetic stir bar was added to the round bottom flask, which was then immersed in an oil bath on top of a magnetic stir plate. Mixing was starting, and the mixture was heated under nitrogen blanket to an internal temperature of 161° C. Initially, the reaction mixture appeared to be a pasty yellow suspension of the triacid 7 in the other molten components. After 50 minutes, the triacid monomer 7 dissolved, and the reaction mixture became a clear yellow solution. A 4.97% solution of tin (II) ethylhexanoate in THF (0.217 g) was added to the solution. The reaction mixture was stirred for 190 minutes under nitrogen resulting in a viscous, yellow liquid that became a tacky solid once cooled to room temperature. HPLC analysis: <0.2 wt. % residual monomer 7. GPC (THF): $M_n$ 2,500, $M_w$ 26,000. $^1$H NMR (400 MHz, CDCl$_3$) δ ppm 12.10-13.72 (1H), 7.29-8.69 (3H), 5.72-6.98 (5H), 3.50-5.57 (14H), 2.02-2.65 (8H), 1.46-1.91 (18H), 1.27 (65H), 0.65-0.96 (9H).

Example 23

Post-Polymerization Modification of Poly(Glyceryl Monostearate/Itaconic Anhydride) with Amine Functionalized Benzotriazole UV-Chromophore In this example, the synthesis of a monoglyceride based polyester containing functionalizable vinylic groups, and covalent attachment of a UV-chromophore to the backbone of the polyester is described. The approach is illustrated in FORMULA IX.

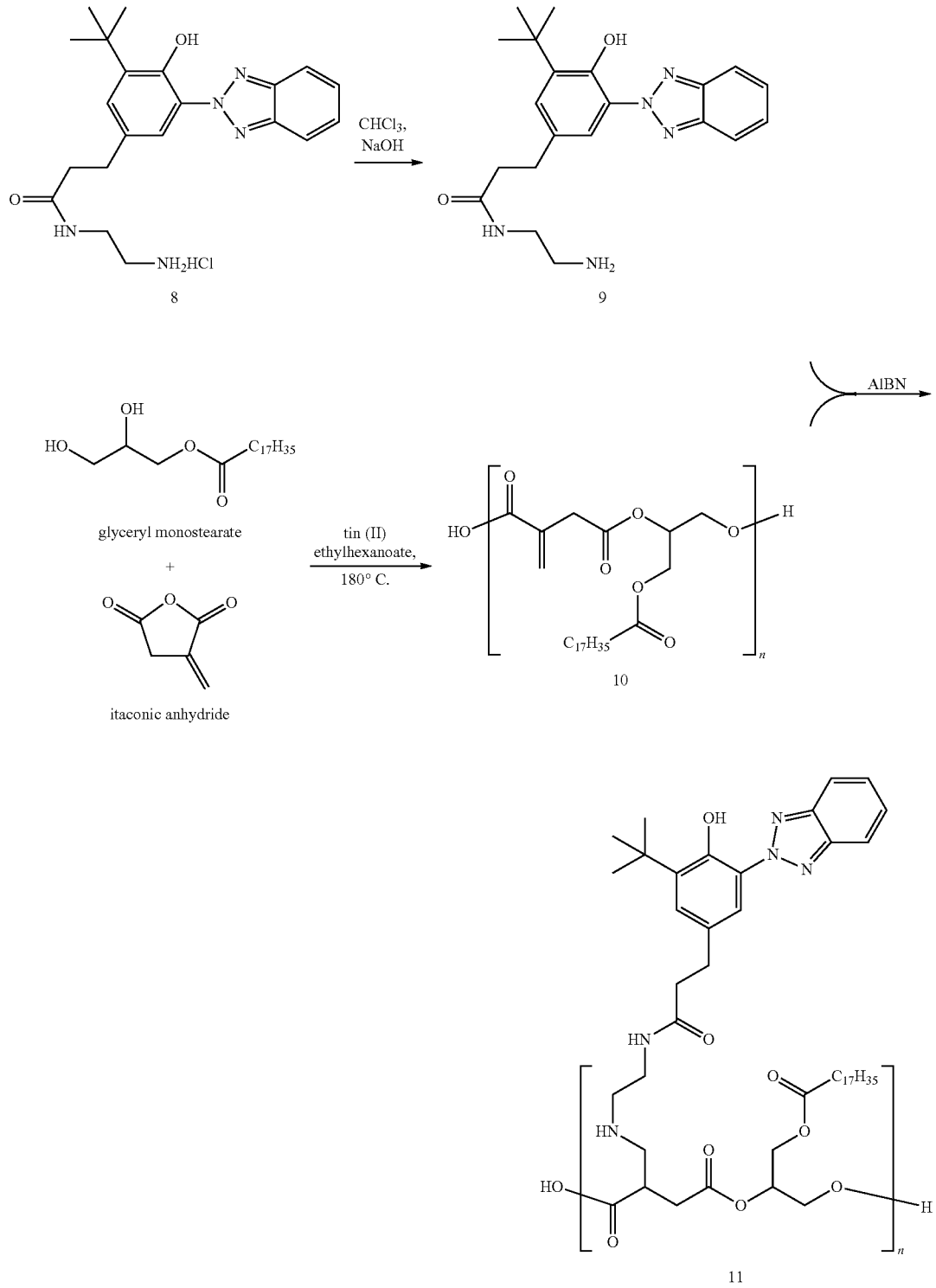

FORMULA IX. POST-POLYMERIZATION FUNCTIONALIZATION

The synthesis of 3-(3-(2H-benzo[d][1,2,3]triazol-2-yl)-5-(tert-butyl)-4-hydroxyphenyl)-N-(2-aminoethyl)propanamide hydrochloride (compound 8) has been described (U.S. Pat. No. 5,166,234). The hydrochloride salt of 8 (5.0 g, 12.0 mmol) was added to a 250 mL separatory funnel with ~75 mL of chloroform ($CHCl_3$). Aqueous NaOH solution (1 M, 50 mL) was added to the funnel. After shaking the mixture, the aqueous layer was removed, and the $CHCl_3$ layer was washed with 2 additional portions of NaOH solution. The $CHCl_3$ layer was washed with portions of brine; the pH of the resulting aqueous layers were monitored using universal indicator strips. Brine washes were repeated until the pH of the aqueous solutions was ~7. The $CHCl_3$ solution was dried over $MgSO_4$, filtered through paper, and concentrated by rotary evaporation; residual solvent was removed under vacuum affording the free base (compound 9). $^1$H NMR (400 MHz, DMSO-$d_6$) δ ppm 8.03-8.11 (m, 1H), 7.94 (d, 1H), 7.81 (t, 1H), 7.53-7.63 (m, 2H), 7.24 (d, 1H), 4.73 (br. s., 3H), 3.04 (q, 2H), 2.87 (t, 2H), 2.52 (t, 2H), 2.42 (t, 2H), 1.37-1.49 (m, 9H).

Glyceryl monostearate (a monoglyceride sold under the trade name MYVEROL 18-06 by Kerry Group plc, Kerry, Ireland; purified by recrystallization from EtOAc; 14.34 g, 40.0 mmol), itaconic anhydride (4.48 g, 40.0 mmol), and tin (II) 2-ethylhexanoate (3.6 µL of a 0.33 molar solution in toluene) were added to a 250 mL single neck round bottom flask containing a magnetic stir bar. The flask was fitted with a distillation adapter with a 100 mL round bottom collection vessel and a connection to a vacuum/nitrogen line. The flask was placed under vacuum and backfilled with nitrogen. The reaction flask was immersed in an oil bath pre-warmed to 185° C.; the mixture was stirred for 24 hours. The material was cooled and removed from the reaction flask by freeze-fracture, then warmed to room temperature under nitrogen. The resulting polymer (10) was an opaque solid with a light tan-orange color and waxy consistency. GPC (THF): $M_n$ 3400, $M_w$ 15700. $^1$H NMR (400 MHz, $CDCl_3$) δ ppm 6.70-6.86, 6.25-6.47, 5.66-6.02, 5.01-5.52, 3.94-4.68, 3.59-3.87, 3.21-3.47, 2.32, 2.18-2.23, 1.97-2.16, 1.49-1.71, 1.26, 0.77-0.98.

Polymer 10 (5.00 g, 11.0 mmol), amine derivatized UV-chromophore 9 (2.11 g, 5.5 mmol) and 2,2'-azobis(2-methylpropionitrile) (AIBN; 82 mg, 0.5 mmol) were added to a 250 mL round bottom flask containing a magnetic stir bar. THF (150 mL) was added to the flask. The flask was fitted with a reflux condenser and then immersed an oil bath pre-warmed to 50° C.; the reaction mixture was stirred for 72 hours. The mixture was then added drop-wise to stirred ice-cold methanol (400 mL); the suspension was placed in a −20° C. freezer for 30 minutes. The methanol was then decanted from the flask and replaced with 200 mL of fresh methanol; the flask was placed in the freezer for 15 minutes. The suspension was vacuum filtered through paper; the precipitate was washed with an additional portion of methanol; residual solvent was removed under reduced pressure at room temperature affording the conjugate 11 as a solid. GPC (THF): $M_n$ 900, $M_w$ 5100. $^1$H NMR (400 MHz, $CDCl_3$) δ ppm 11.45-11.98 (1H), 7.99-8.22 (1H), 7.74-7.99 (2H), 7.37-7.56 (2H), 7.08-7.25 (1H), 6.68-6.92 (1H), 5.63-6.49 (2H), 4.91-5.51 (3H), 4.18 (22H), 3.11-3.88 (16H), 2.86-3.10 (5H), 2.42-2.84 (10H), 2.19-2.42 (15H), 1.70-2.19 (6H), 0.96-1.70 (193H), 0.89 (19H).

Example 24

Conversion of Benzotriazole Carboxylate to Acid Chloride 12 (3-(3-(2H-benzo[d][1,2,3]triazol-2-yl)-5-(tert-butyl)-4-hydroxyphenyl)propanoyl chloride)

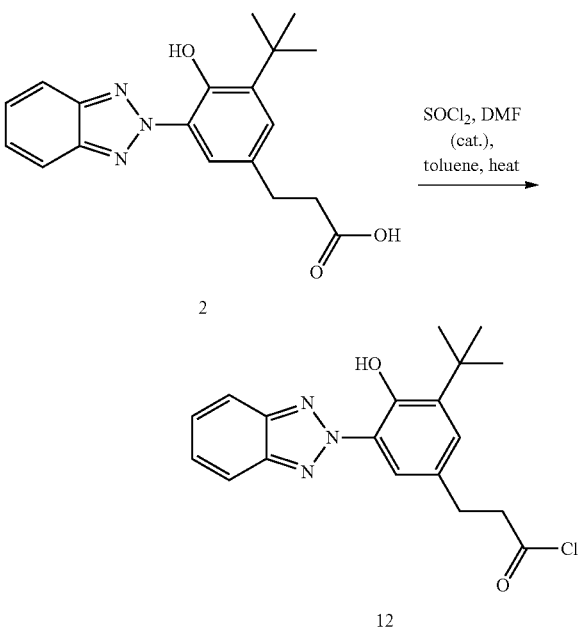

FORMULA X. CONVERSION OF CARBOXYLATE 2 TO ACID CHLORIDE 12

The conversion of the benzotriazole carboxylic acid 2 to the corresponding acid chloride 12 is illustrated in FORMULA X. Compound 2 (50 g 147 mmol, synthesized as described in Example 1) was added to a 1000 mL 3-neck flask containing a magnetic stir bar; the flask was equipped with a reflux condenser, nitrogen inlet, and rubber septum. Anhydrous toluene (~500 mL) was transferred into the flask by cannula through the septa. Thionyl chloride (16.1 mL, 221 mmol) was transferred into the flask by syringe; DMF (2.7 mL) was then added to the flask by syringe. The flask was immersed in an oil bath set at 80° C.; the suspension was stirred; the solids began to disperse, eventually yielding a clear solution. After ~4 hours, the reaction mixture was allowed to cool, transferred to a round bottom flask and concentrated by rotary evaporation. The resulting oil was triturated with hexanes, affording a beige solid. The suspension of material was recrystallized by adding additional hexanes and warming to reflux, filtration through paper, and slow cooling to room temperature with stirring. The resulting beige crystals were filtered and dried under vacuum at 50° C. The filtrate was concentrated, and the recrystallization performed a second time affording a second crop of crystals; the mass of the combined crops of compound 12 was 44.7 grams. $^1$H NMR (400 MHz, $CDCl_3$) δ 11.88 (s, 1H), 8.16 (d, J=2.2 Hz, 1H), 7.91-7.98 (m, 2H), 7.47-7.54 (m, 2H), 7.21 (d, J=2.2 Hz, 1H), 3.29 (t, J=7.5 Hz, 2H), 3.07 (t, J=7.5 Hz, 2H), 1.50-1.53 (s, 9H).

Example 25

Conversion of Benzotriazole Acid Chloride 12 to Isocyanate 13 (2-(2H-benzo[d][1,2,3]triazol-2-yl)-6-(tert-butyl)-4-(2-isocyanatoethyl)phenol)

FORMULA XI. CONVERSION OF ACID CHLORIDE 12 TO ISOCYANATE 13

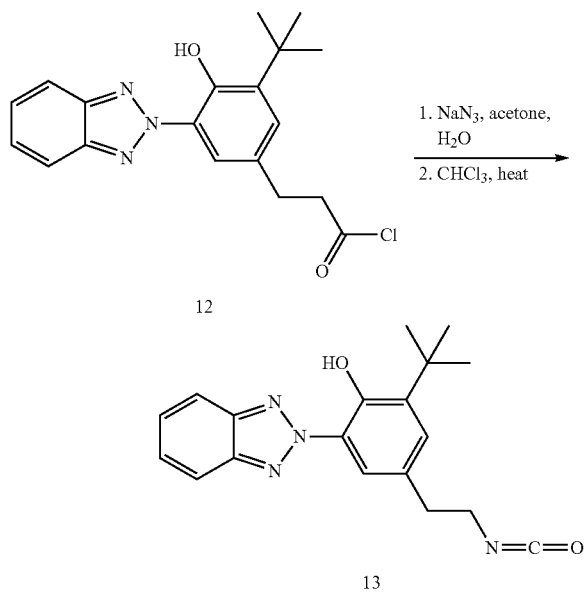

Sodium azide (NaN$_3$, 2.5 g, 38 mmol: CAUTION! NaN$_3$ is a violent poison) was carefully transferred into a single necked 500 mL round bottom flask containing a magnetic stir bar. Deionized water (20 mL) was added to the flask; the NaN$_3$ dissolved with mixing affording a clear solution. The flask was immersed in an ice bath. Acid chloride 12 (7.0 g 20 mmol) and anhydrous acetone (45 mL) were transferred into a pressure equalizing addition funnel in a positive pressure N$_2$ atmosphere glove box. The acid chloride dissolved in the acetone with gentle swirling, affording a clear yellow solution. The addition funnel containing 12 was fitted into the flask containing the aqueous solution of NaN$_3$; the top of the addition funnel was fitted with a N$_2$ adapter connected to a Schlenk line. The solution of 12 was added dropwise to the NaN$_3$ solution. After addition of several drops, a white precipitate began to appear, suspended in the aqueous solution. Complete addition of 12 was complete within 30 minutes; mixing was continued for 20 minutes in the ice bath. Water (30 mL) was added to the resulting white slurry; solids were collected by filtration through a glass frit under vacuum. The white solid was transferred to a separatory funnel followed with CHCl$_3$ (185 mL). The flask was shaken and the layers were allowed to separate. The lower organic phase was removed from the small aqueous layer and dried over Na$_2$SO$_4$. The solution was filtered; the filtrate was placed in a single necked 500 mL round bottom flask containing a magnetic stir bar; the flask was fitted with a reflux condenser with nitrogen inlet adapter and immersed in an oil bath. The solution was heated slowly, with mixing, to reflux, over 30 minutes. The final oil bath temperature was 65° C. As the oil bath temperature surpassed 55° C., bubbling was apparent in the solution. The reaction was allowed to reflux for a total of 90 min. CHCl$_3$ was then removed by rotary evaporation; the resulting oil crystallized overnight on standing affording the product 12 (5.8 g) as a slightly grey solid. $^1$H NMR (400 MHz, CDCl$_3$) δ 11.91 (s, 1H), 8.18 (d, J=1.9 Hz, 1H), 7.92-7.98 (m, 2H), 7.47-7.53 (m, 2H), 7.23 (d, J=2.1 Hz, 1H), 3.59 (t, J=6.9 Hz, 2H), 2.96 (t, J=6.9 Hz, 2H), 1.52 (s, 9H).

Example 26

Summary of SPF Results

The in vitro SPF measurement results for a selection of polymers described in the previous examples are summarized in Table 1. The in vitro test method employed for the measurement of the polymer samples is described in Example 3.

TABLE 1

Summary of in vitro SPF testing results for select examples

| Example # | Vehicle | wt. % polymer in vehicle | in vitro SPF |
|---|---|---|---|
| 3 | FINSOLV TN | 50 | 17.5 |
|   | FINSOLV TN | 40 | 12.7 |
|   | FINSOLV TN | 30 | 11.3 |
|   | FINSOLV TN | 20 | 10.7 |
|   | FINSOLV TN | 10 | 6.0 |
| 4 | FINSOLV TN | 29 | 19.3 |
|   | FINSOLV TN | 40 | 29.0 |
| 5 | FINSOLV TN | 19 | 16 |
|   | FINSOLV TN | 38 | 22.7 |
| 6 | FINSOLV TN | 20 | 10.4 |
| 7 | FINSOLV TN | 20 | 10.6 |
|   | FINSOLV TN | 40 | 15.0 |
| 8 | FINSOLV TN | 10 | 5.0 |
|   | FINSOLV TN | 21 | 11.0 |
|   | FINSOLV TN | 29 | 14.0 |
|   | FINSOLV TN | 40 | 17.0 |
| 9 | FINSOLV TN | 34 | 14.7 |
|   | FINSOLV TN | 20 | 13.7 |
| 10 | FINSOLV TN | 40 | 44.0 |
|   | FINSOLV TN | 35 | 20.0 |
|   | FINSOLV TN | 25 | 15.0 |
| 11 | FINSOLV TN | 40 | 22.0 |
|   | FINSOLV TN | 20 | 9.0 |
|   | FINSOLV TN | 10 | 6.0 |
| 12 | FINSOLV TN | 40 | 22.0 |
|   | FINSOLV TN | 75 | 155.0 |
| 13 | FINSOLV TN | 63 | 76.0 |
| 14 | FINSOLV TN | 58 | 118.0 |
|   | FINSOLV TN | 40 | 16.0 |
| 18 | FINSOLV TN | 20 | 23.0 |
| 20 | FINSOLV TN | 39 | >500 |

We claim:

1. An ultraviolet radiation absorbing polymer composition comprising the reaction product of a monoglyceride and a poly-acid monomer containing a UV-chromophore selected from the group consisting of triazoles; dibenzoylmethanes; 4-aminobenzoic acid and alkane esters thereof; anthranilic acid and alkane esters thereof; salicylic acid and alkane esters thereof; hydroxycinnamic acid and alkane esters thereof; dihydroxy, dicarboxy, or hydroxycarboxybenzophenones and alkane ester or acid halide derivatives thereof; dihydroxy, dicarboxy, or hydroxycarboxychalcones and alkane ester or acid halide derivatives thereof; dihydroxy, dicarboxy, or hydroxycarboxycoumarins and alkane ester or acid halide derivatives thereof; benzimidazole derivatives; benzoxazole derivatives; 3-(3-(2H-benzo[d][1,2,3]triazol-2-yl)-5-(tert-butyl)-4-hydroxyphenyl); 6-octyl-2-(4-(4,6-di([1, 1'-biphenyl]-4-yl)-1,3,5-triazin-2-yl)-3-hydroxyphenoxy) propanoate and trioctyl 2,2',2"-(((1,3,5-triazine-2,4,6-triyl) tris(3-hydroxybenzene-4,1-diyl))tris(oxy))tripropanoate.

2. The composition of claim 1, wherein the monoglyceride is selected from the group consisting of glycerol monostearate, glycerol monopalmitate, glycerol monomyristate, glycerol monocaprate, glycerol monodecanoate, glycerol monolaurate, glycerol monolinoleate, and glycerol monooleate.

3. The composition of claim 1, comprising the reaction product of said monoglyceride, said poly-acid monomer containing said UV-chromophore and a poly-ol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s glycols, polyglycerols, polyglycerol esters, glycerol, monosaccharide, disaccharides, polysaccharides, and linear polysiloxanes end-functionalized with carbinol groups.

4. The composition of claim 1, wherein the polymer composition is a reaction product of said monoglyceride, said poly-acid monomer containing said UV-chromophore and a poly-acid selected from the group consisting of natural multifunctional carboxylic acid, hydroxy acid and unsaturated acid; wherein the natural multifunctional carboxylic acid is selected from the group consisting of succinic, glutaric, adipic, pimelic, suberic, and sebacic acids; wherein the hydroxy acid is selected from the group consisting of diglycolic, malic, tartaric and citric acids; wherein the unsaturated acid is selected from the group consisting of fumaric acid and maleic acid.

5. The composition of claim 1, wherein the ultraviolet radiation absorbing polymer composition has a weight average molecular weight from about 500 to about 50,000.

6. An ultraviolet radiation absorbing polymer composition comprising a polymer comprising a repeat unit

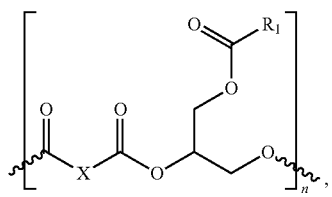

wherein X comprises a UV chromophore selected from the group consisting of triazoles; dibenzoylmethanes; 4-aminobenzoic acid and alkane esters thereof; anthranilic acid and alkane esters thereof; salicylic acid and alkane esters thereof; hydroxycinnamic acid and alkane esters thereof; dihydroxy, dicarboxy, or hydroxycarboxybenzophenones and alkane ester or acid halide derivatives thereof; dihydroxy, dicarboxy, or hydroxycarboxychalcones and alkane ester or acid halide derivatives thereof; dihydroxy, dicarboxy, or hydroxycarboxycoumarins and alkane ester or acid halide derivatives thereof; benzimidazole derivatives; benzoxazole derivatives; 3-(3-(2H-benzo[d][1,2,3]triazol-2-yl)-5-(tert-butyl)-4-hydroxyphenyl); 6-octyl-2-(4-(4,6-di([1,1'-biphenyl]-4-yl)-1,3,5-triazin-2-yl)-3-hydroxyphenoxy)propanoate and trioctyl 2,2',2"-(((1,3,5-triazine-2,4,6-triyl)tris(3-hydroxybenzene-4,1-diyl))tris(oxy))tripropanoate, and $R_1$ is a saturated or unsaturated hydrocarbon moiety having a number of carbon atoms between 4 and 30.

7. The ultraviolet radiation absorbing polymer composition of claim 6, comprising a polymer having the structure

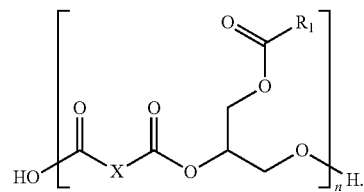

8. The ultraviolet radiation absorbing polymer composition of claim 6, wherein n is a number such that the ultraviolet radiation absorbing polymer composition has a weight average molecular weight from about 500 to about 50,000.

9. A composition comprising a cosmetically acceptable topical carrier and an ultraviolet radiation absorbing polymer composition that comprises the reaction product of a monoglyceride and a poly-acid monomer containing a UV-chromophore selected from the group consisting of triazoles; dibenzoylmethanes; 4-aminobenzoic acid and alkane esters thereof; anthranilic acid and alkane esters thereof; salicylic acid and alkane esters thereof; hydroxycinnamic acid and alkane esters thereof; dihydroxy, dicarboxy, or hydroxycarboxybenzophenones and alkane ester or acid halide derivatives thereof; dihydroxy, dicarboxy, or hydroxycarboxychalcones and alkane ester or acid halide derivatives thereof; dihydroxy, dicarboxy, or hydroxycarboxycoumarins and alkane ester or acid halide derivatives thereof; benzimidazole derivatives; benzoxazole derivatives; 3-(3-(2H-benzo[d][1,2,3]triazol-2-yl)-5-(tert-butyl)-4-hydroxyphenyl); 6-octyl-2-(4-(4,6-di([1,1'-biphenyl]-4-yl)-1,3,5-triazin-2-yl)-3-hydroxyphenoxy)propanoate and trioctyl 2,2',2"-(((1,3,5-triazine-2,4,6-triyl)tris(3-hydroxybenzene-4,1-diyl))tris(oxy))tripropanoate.

10. A composition comprising a cosmetically acceptable topical carrier and an ultraviolet radiation absorbing polymer composition comprising a polymer comprising a repeat unit:

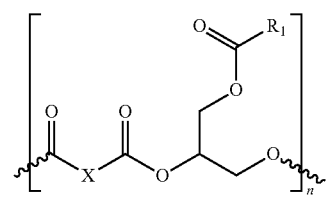

wherein X comprises a UV chromophore selected from the group consisting of triazoles; dibenzoylmethanes; 4-aminobenzoic acid and alkane esters thereof; anthranilic acid and alkane esters thereof; salicylic acid and alkane esters thereof; hydroxycinnamic acid and alkane esters thereof; dihydroxy, dicarboxy, or hydroxycarboxybenzophenones and alkane ester or acid halide derivatives thereof; dihydroxy, dicarboxy, or hydroxycarboxychalcones and alkane ester or acid halide derivatives thereof; dihydroxy, dicarboxy, or hydroxycarboxycoumarins and alkane ester or acid halide derivatives thereof; benzimidazole derivatives; benzoxazole derivatives; 3-(3-(2H-benzo[d][1,2,3]triazol-2-yl)-5-(tert-butyl)-4-hydroxyphenyl); 6-octyl-2-(4-(4,6-di([1,1'-biphenyl]-4-yl)-1,3,5-triazin-2-yl)-3-hydroxyphenoxy)propanoate and trioctyl 2,2',2"-(((1,3,5-triazine-2,4,6-triyl)tris(3-hydroxybenzene-4,1-diyl))tris(oxy))tripropanoate.

11. The composition of claim 1 wherein the monoglyceride is a $C_{12}$-$C_{18}$ monoglyceride.

12. The composition of claim 9 wherein the monoglyceride is a $C_{12}$-$C_{18}$ monoglyceride.

* * * * *